United States Patent
Sato

(10) Patent No.: US 11,406,267 B2
(45) Date of Patent: Aug. 9, 2022

(54) CARTILAGE-TISSUE ANALYSIS DEVICE

(71) Applicant: OLYMPUS CORPORATION, Tokyo (JP)

(72) Inventor: Akira Sato, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 664 days.

(21) Appl. No.: 16/507,186

(22) Filed: Jul. 10, 2019

(65) Prior Publication Data

US 2019/0343394 A1 Nov. 14, 2019

Related U.S. Application Data

(63) Continuation of application No. PCT/JP2017/002003, filed on Jan. 20, 2017.

(51) Int. Cl.
*A61B 5/00* (2006.01)
*G01N 21/65* (2006.01)
*A61B 10/00* (2006.01)

(52) U.S. Cl.
CPC .......... *A61B 5/0075* (2013.01); *A61B 5/4514* (2013.01); *G01N 21/65* (2013.01); *A61B 10/00* (2013.01); *G01N 2021/656* (2013.01)

(58) Field of Classification Search
CPC ..... A61B 5/0075; A61B 5/4514; A61B 10/00; A61B 2562/0233; A61B 2562/043; G01N 21/65; G01N 2021/656
See application file for complete search history.

(56) References Cited

U.S. PATENT DOCUMENTS 7,729,749 B2 6/2010 Roessler et al.
2002/0002336 A1 * 1/2002 Marchitto .............. G01N 21/65
600/473

(Continued)

FOREIGN PATENT DOCUMENTS

JP 2008-522697 A 7/2008
JP 2009-508571 A 3/2009

(Continued)

OTHER PUBLICATIONS

International Search Report dated Apr. 11, 2017 issued in PCT/JP2017/002003.

(Continued)

*Primary Examiner* — Dominic J Bologna
(74) *Attorney, Agent, or Firm* — Scully, Scott, Murphy & Presser, P.C.

(57) ABSTRACT

A cartilage-tissue analysis device includes: an illuminating fiber that emits, from a light-emission surface thereof, laser light coming from a laser light source; two light-collecting fibers that receives scattered light at respective light-receiving surfaces the distances from which to the light-emission surface differ from each other; and detector that detects Raman spectra from the scattered light received by the light-collecting fibers. The cartilage-tissue analysis device is configure to: calculate an intensity ratio between two Raman bands originating from cartilage tissue and subchondral bone tissue, respectively, from each of the two Raman spectra; and evaluate a state of the cartilage tissue by selecting, from among the two Raman spectra, a Raman spectrum the intensity ratio of which is within a prescribed range and that analyzes the selected Raman spectrum, to analyze the selected Raman spectrum.

15 Claims, 23 Drawing Sheets

(56) References Cited

U.S. PATENT DOCUMENTS

| | | | |
|---|---|---|---|
| 2002/0091322 A1* | 7/2002 | Chaiken | A61B 5/442 600/476 |
| 2005/0119587 A1* | 6/2005 | Roessler | G01N 21/65 600/562 |
| 2007/0049808 A1* | 3/2007 | Roessler | A61B 5/0059 600/315 |
| 2007/0082409 A1* | 4/2007 | Morris | G01J 3/02 436/171 |
| 2008/0076985 A1* | 3/2008 | Matousek | A61B 5/0059 600/310 |
| 2009/0219523 A1 | 9/2009 | Morris et al. | |
| 2011/0178379 A1* | 7/2011 | Dudhia | A61P 19/02 514/42 |

FOREIGN PATENT DOCUMENTS

| | | |
|---|---|---|
| JP | 2009-538156 A | 11/2009 |
| WO | 03/087793 A1 | 10/2003 |
| WO | WO 2006/061565 A1 | 6/2006 |
| WO | WO 2007/040589 A1 | 4/2007 |
| WO | WO 2007/113570 A1 | 10/2007 |
| WO | WO 2016/051763 A1 | 4/2016 |

OTHER PUBLICATIONS

Esmonde-White, Karen A. et al., "Fiber-optic Raman Spectroscopy of Joint Tissues", NIH Public Access Author Manuscript, Analyst (Apr. 21, 2011), vol. 136, No. 8, pp. 1675-1685, cited in ISR and spec on p. 3.

Afara, I. et al., "Non-destructive evaluation of articular cartilage defects using near-infrared (NIR) spectroscopy in osteoarthritic rat models and its direct relation to Mankin score", Osteoarthritis and Cartilage (Nov. 2012), vol. 20, pp. 1367-1373, cited in spec on p. 4.

* cited by examiner

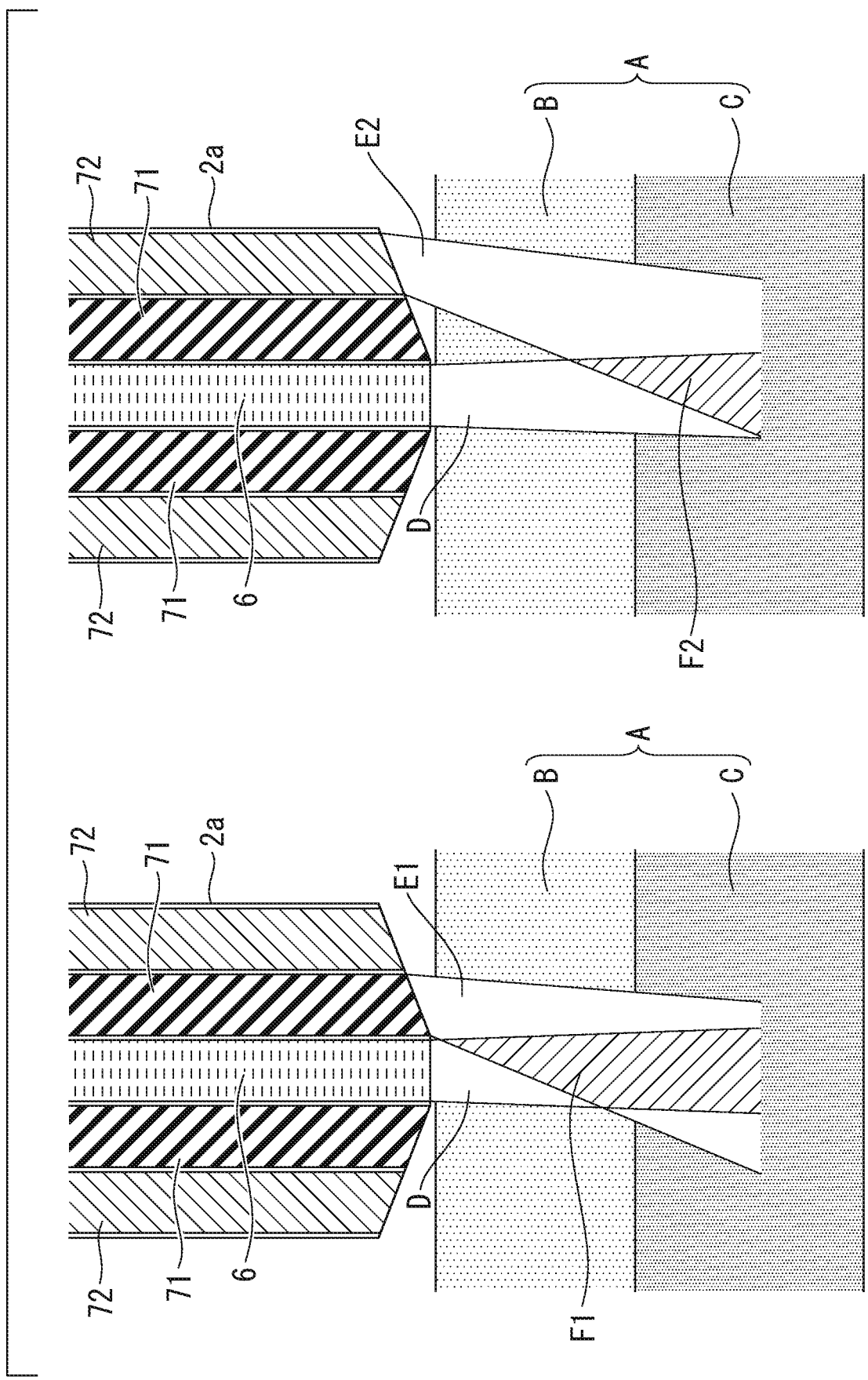

CARTILAGE-TISSUE ANALYSIS DEVICE

CROSS-REFERENCE TO RELATED APPLICATIONS

This is a continuation of International Application PCT/JP2017/002003, with an international filing date of Jan. 20, 2017, which is hereby incorporated by reference herein in its entirety.

TECHNICAL FIELD

The present invention relates to a cartilage-tissue analysis device.

BACKGROUND ART

X-ray images, nuclear magnetic resonance images, and arthroscopy have been used to diagnose cartilage damage due to osteoarthritis (OA), which involves lesioning of articular cartilage, or an external injury and to diagnose regenerated cartilage after regenerative treatment by implantation of cultured cartilage cells. Recently, a method has been proposed for optically evaluating the state of cartilage by performing near infrared light spectrometry based on, for example, the diffuse reflection method or the Raman scattering method with a small-diameter optical fiber probe and by acquiring information about changes in articular cartilage matrices, such as collagen and glycosaminoglycan (GAG) (refer to, for example, NPL 1, NPL 2, and PTL 1).

An epiphysis is composed of cartilage tissue covering the bone surface and subchondral bone tissue lying underneath the cartilage tissue. Cartilage tissue is hyaline cartilage, and its principal components are type II collagen, glycosaminoglycan (GAG) such as chondroitin sulfate, and water. In addition, the principal components of subchondral bone tissue are type I collagen, calcium phosphate such as hydroxyapatite, and calcium carbonate. The thickness of human cartilage tissue is about 2 to 4 mm in the case of normal cartilage, and human cartilage tissue is known to readily become thinner as lesioning, such as osteoarthritis, progresses. In proposed methods for optically evaluating cartilage properties, optical spectra originating from cartilage tissue and subchondral bone tissue are measured at an end of the epiphysis. For example, in the device in PTL 1, Raman spectra originating from cartilage tissue and subchondral bone tissue of an epiphysis are measured, and the state of cartilage tissue is evaluated on the basis of information about particular Raman bands in those Raman spectra.

For example, FIG. 8 of PTL 1 shows a method for diagnosing osteoarthritis (OA) on the basis of the intensity ratio between Raman bands of calcium phosphate and calcium carbonate contained in subchondral bone tissue. In addition, FIG. 9 of PTL 1 shows a method for diagnosing osteoarthritis (OA) on the basis of the intensity ratios between Raman bands of calcium carbonate and calcium phosphate and furthermore a Raman band originating from a CH group in protein.

Furthermore, FIG. 19 of PTL 1 shows a method for diagnosing OA on the basis of the intensity ratio between two amide III bands at 1240 $cm^{-1}$ and 1270 $cm^{-1}$, which are known to correlate with a change in the molecular structure of collagen, i.e., collagen denaturation.

CITATION LIST

Patent Literature

{PTL 1}
 U.S. Pat. No. 7,729,749

{Non Patent Literature}

{NPL 1}
 Karen A. Esmonde-White et al., "Fiber-optic Raman Spectroscopy of Joint Tissues", Analyst, April 2011, Vol. 136, p. 1675-1685

{NPL 2}
 I. Afara et al., "Non-destructive evaluation of articular cartilage defects using near-infrared spectroscopy in osteoarthritic rat models and its direct relation to Mankin score", Osteoarthritis and Cartilage, November 2012, Vol. 20, p. 1367-1373

SUMMARY OF INVENTION

One aspect of the present invention is a cartilage-tissue analysis device including: a laser light source that outputs laser light; an illuminating fiber having a light-emission surface at a distal end thereof, said illuminating fiber emitting, from the light-emission surface towards biological tissue including cartilage tissue, the laser light that is incident thereon from the laser light source; a first light-collecting fiber and a second light-collecting fiber each having a light-receiving surface at a distal end thereof and each receiving scattered light from the biological tissue at the light-receiving surface; and a detector that detects a first Raman spectrum from the scattered light received by the first light-collecting fiber and that detects a second Raman spectrum from the scattered light received by the second light-collecting fiber, wherein the cartilage-tissue analysis device is configured to: calculate, from each of the first Raman spectrum and the second Raman spectrum detected by the detector, an intensity ratio between a Raman band originating from the cartilage tissue and a Raman band originating from subchondral bone tissue; and evaluate a state of the cartilage tissue by selecting, from among the first Raman spectrum and the second Raman spectrum, a Raman spectrum the calculated intensity ratio of which is within a prescribed range, to analyze the selected Raman spectrum, and wherein a distance from the light-emission surface to the light-receiving surface of the first light-collecting fiber differs from a distance from the light-emission surface to the light-receiving surface of the second light-collecting fiber.

BRIEF DESCRIPTION OF DRAWINGS

FIG. 13A is a diagram for illustrating positional relationships between cartilage tissue and examination areas in a case where the tissue thickness of the cartilage tissue for the examination areas is between the thickness in the case of FIG. 11A and the thickness in the case of FIG. 12A.

DESCRIPTION OF EMBODIMENTS

A cartilage-tissue analysis device 100 according to one embodiment of the present invention will now be described with reference to the drawings.

Figure 1:
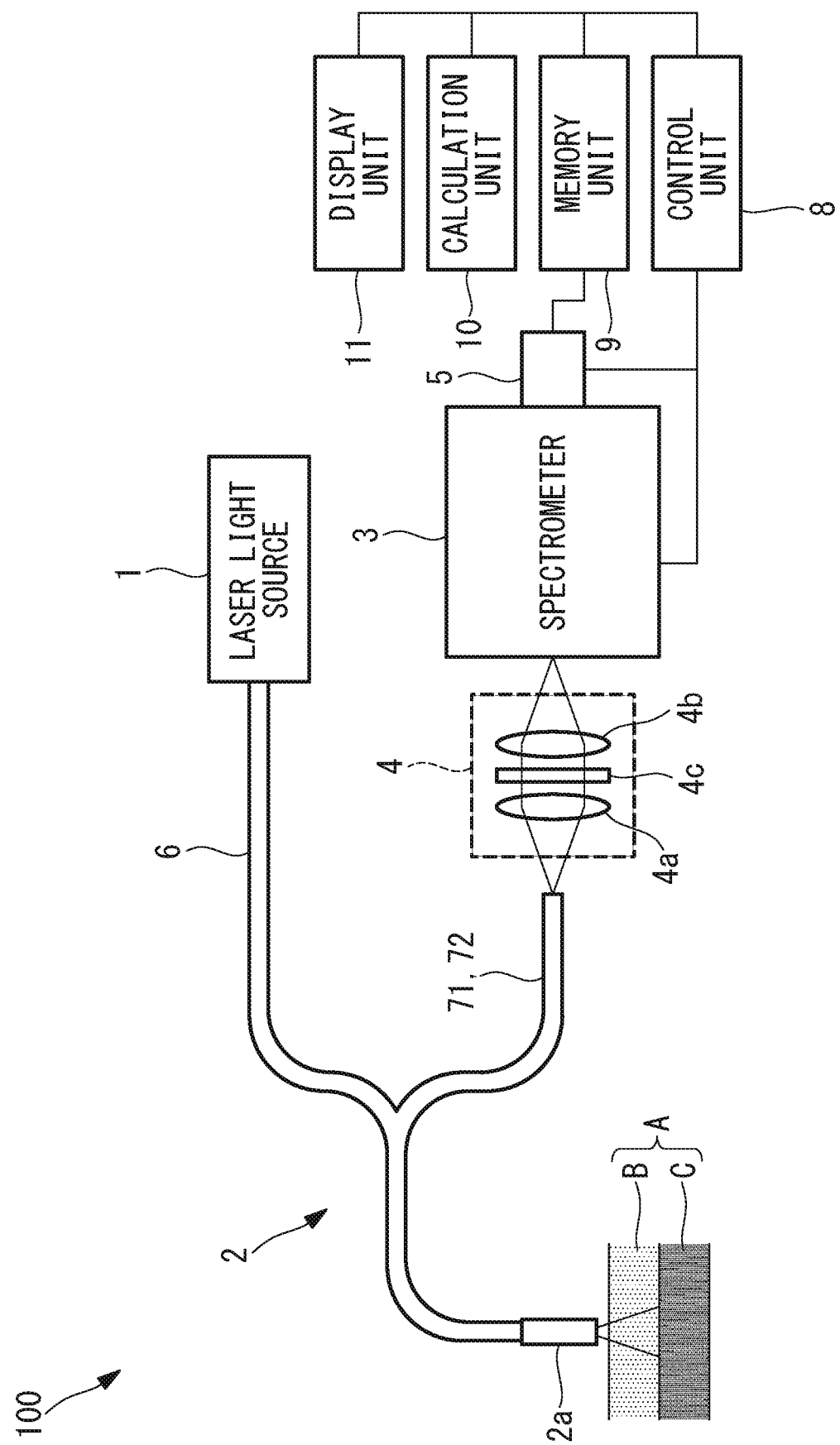
FIG. 1 is an overall configuration diagram of a cartilage-tissue analysis device according to one embodiment of the present invention.

As shown in FIG. 1, the cartilage-tissue analysis device 100 according to this embodiment includes: a laser light source 1; an optical probe 2 that radiates laser light coming from the laser light source 1 onto an epiphysis (biological tissue) A and that receives Raman scattered light from the epiphysis A; a spectrometer (detection unit) 3 for spectrally dispersing the Raman scattered light received by the optical probe 2; a coupling optical system 4 disposed between the optical probe 2 and the spectrometer 3; and a photodetector (detection unit) 5 that detects the light spectrally dispersed by the spectrometer 3 and that acquires a Raman spectrum.

The laser light source 1 is a semiconductor laser for outputting near-infrared laser light having a wavelength of 785 nm. Light from the laser light source 1 may have a wavelength other than 785 nm.

The optical probe 2 includes: an illuminating fiber 6 for guiding laser light from the laser light source 1; and first light-collecting fibers 71 and second light-collecting fibers 72 for receiving and guiding Raman scattered light. The illuminating fiber 6 and the light-collecting fibers 71 and 72 are bundled into one on the distal end side, and the distal end portion of the illuminating fiber 6 and the distal end portions of the light-collecting fibers 71 and 72 are housed in a probe head 2a at the distal end portion of the optical probe 2. The illuminating fiber 6 and the light-collecting fibers 71 and 72 are split off from each other at an intermediate position in the longitudinal direction, the basal end of the illuminating fiber 6 is connected to the laser light source 1, and the basal ends of the light-collecting fibers 71 and 72 are optically coupled to the spectrometer 3 via the coupling optical system 4.

Laser light that is incident on the illuminating fiber 6 from the laser light source 1 is guided by the illuminating fiber 6 and is emitted from the probe head 2a towards the epiphysis A. In addition, Raman scattered light excited in the epiphysis A as a result of being irradiated with the laser light is collected by the light-collecting fibers 71 and 72, is guided by the light-collecting fibers 71 and 72 and coupling optical system 4, and is then incident on the spectrometer 3.

The coupling optical system 4 can be a collimating optical system includes a combination of: a lens 4a for converting, into collimated light, the light emitted as diverging light from the basal ends of the light-collecting fibers 71 and 72; and a lens 4b for forming an image of the collimated light, which has been converted by the lens 4a, at the position of an inlet slit of the spectrometer 3. Between the lenses 4a and 4b is an optical filter 4c that blocks reflected light of laser light L and that transmits Raman scattered light having a wavelength larger than the wavelength of the laser light.

The spectrometer 3 spatially disperses, by wavelength, light that is incident thereon from the light-collecting fibers 71 and 72 via the coupling optical system 4 and re-forms an image of the obtained spectrum on a light-receiving surface of the photodetector 5.

The photodetector 5 can be a camera provided with an image capturing element in which photoelectric conversion elements, such as CCD elements, are arrayed two-dimensionally and is attached to the spectrometer 3. The photodetector 5 converts, into an electrical signal by means of the photoelectric conversion elements, light emitted from the spectrometer 3 and incident on the light-receiving surface thereof and acquires data on the Raman spectrum.

Next, a detailed configuration of the optical probe 2 will be described.

Figure 2:
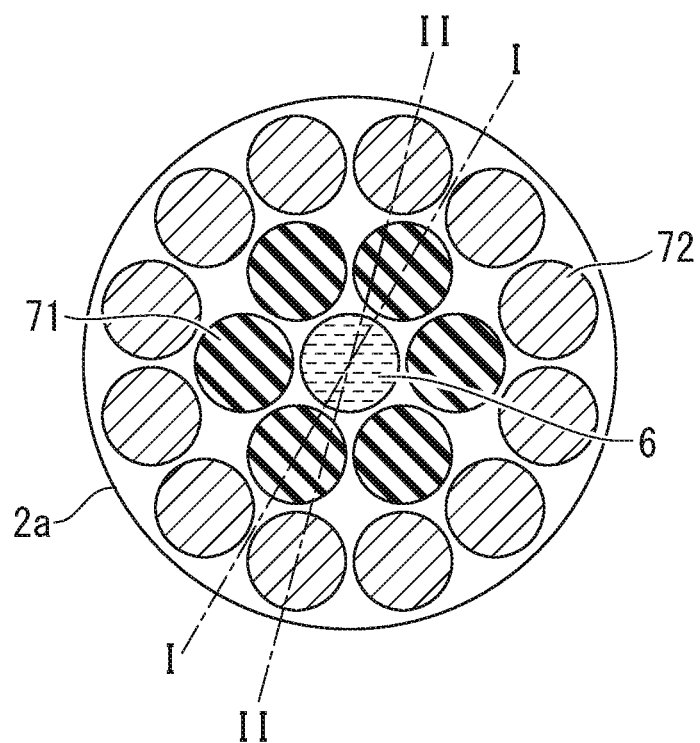
FIG. 2 is a transverse sectional view of the distal end portion of an optical probe in FIG. 1.
Figure 3:
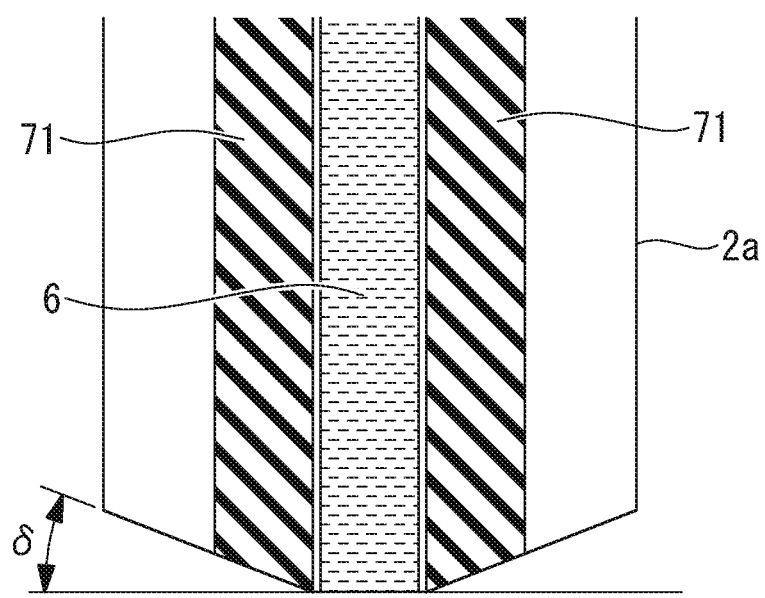
FIG. 3 is a longitudinal sectional view taken along line I-I of the optical probe in FIG. 2.
Figure 4:
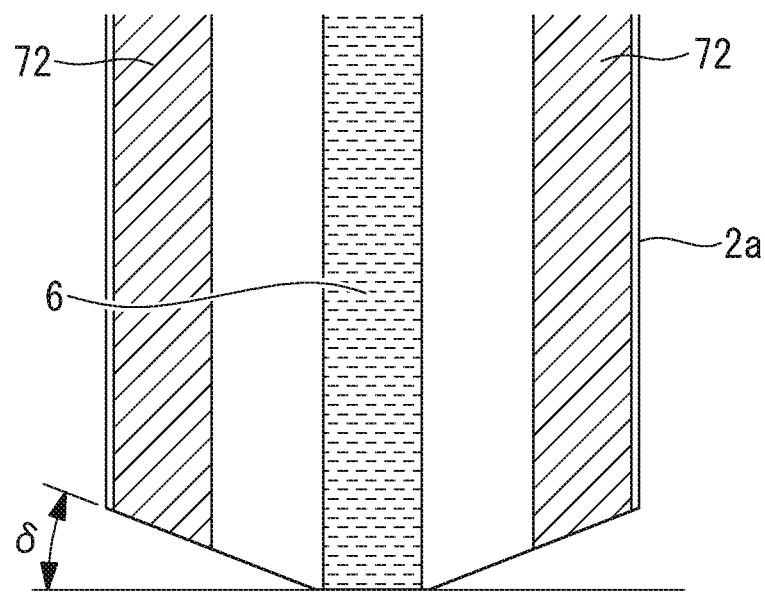
FIG. 4 is a longitudinal sectional view taken along line II-II of the optical probe in FIG. 2.

As shown in FIGS. 2 to 4, the optical probe 2 includes: the one illuminating fiber 6; the plurality of first light-collecting fibers 71; and the plurality of second light-collecting fibers 72. FIG. 2 shows a transverse section of the probe head 2a (cross section of the optical probe 2 orthogonal to the longitudinal direction thereof), and FIGS. 3 and 4 show longitudinal cross sections of the probe head 2a (cross sections of the optical probe 2 along the longitudinal thereof) taken along line I-I and line II-II, respectively, in FIG. 2.

The illuminating fiber 6 and the light-collecting fibers 71 and 72 are, for example, optical fibers that have a core diameter of 105 μm or 200 μm and a clad diameter of 125 μm or 240 μm and that are made of silica with a small hydroxyl group content. It is preferable that the numerical aperture NA of the illuminating fiber 6 be 0.22 or more and that the numerical apertures NA of the light-collecting fibers 71 and 72 be 0.22 or less.

As shown in FIGS. 3 and 4, in the probe head 2a, the illuminating fiber 6 and the light-collecting fibers 71 and 72 are arranged so as to be parallel to one another along the longitudinal direction of the probe head 2a. The first light-collecting fibers 71 and the second light-collecting fibers 72 are arranged so as to form concentric circles with the illuminating fiber 6 disposed at the center, wherein the first light-collecting fibers 71 form the radially inward circle and the second light-collecting fibers 72 form the radially outward circle. Therefore, the radial distance from the distal end surface (light-emission surface) of the illuminating fiber 6 to the distal end surface (light-receiving surface) of each of the first light-collecting fibers 71 is smaller than the radial distance from the distal end surface of the illuminating fiber 6 to the distal end surface (light-receiving surface) of each of the second light-collecting fibers 72.

As shown in FIGS. 3 and 4, the distal end surface of the illuminating fiber 6 is orthogonal to the longitudinal direction of the probe head 2a. Therefore, as shown FIGS. 5 and 6, laser light emitted from the distal end surface of the illuminating fiber 6 at a prescribed numerical aperture is radiated on a conical illumination region D in front of the distal end of the probe head 2a, and Raman scattered light is generated in the illumination region D.

Figure 5:
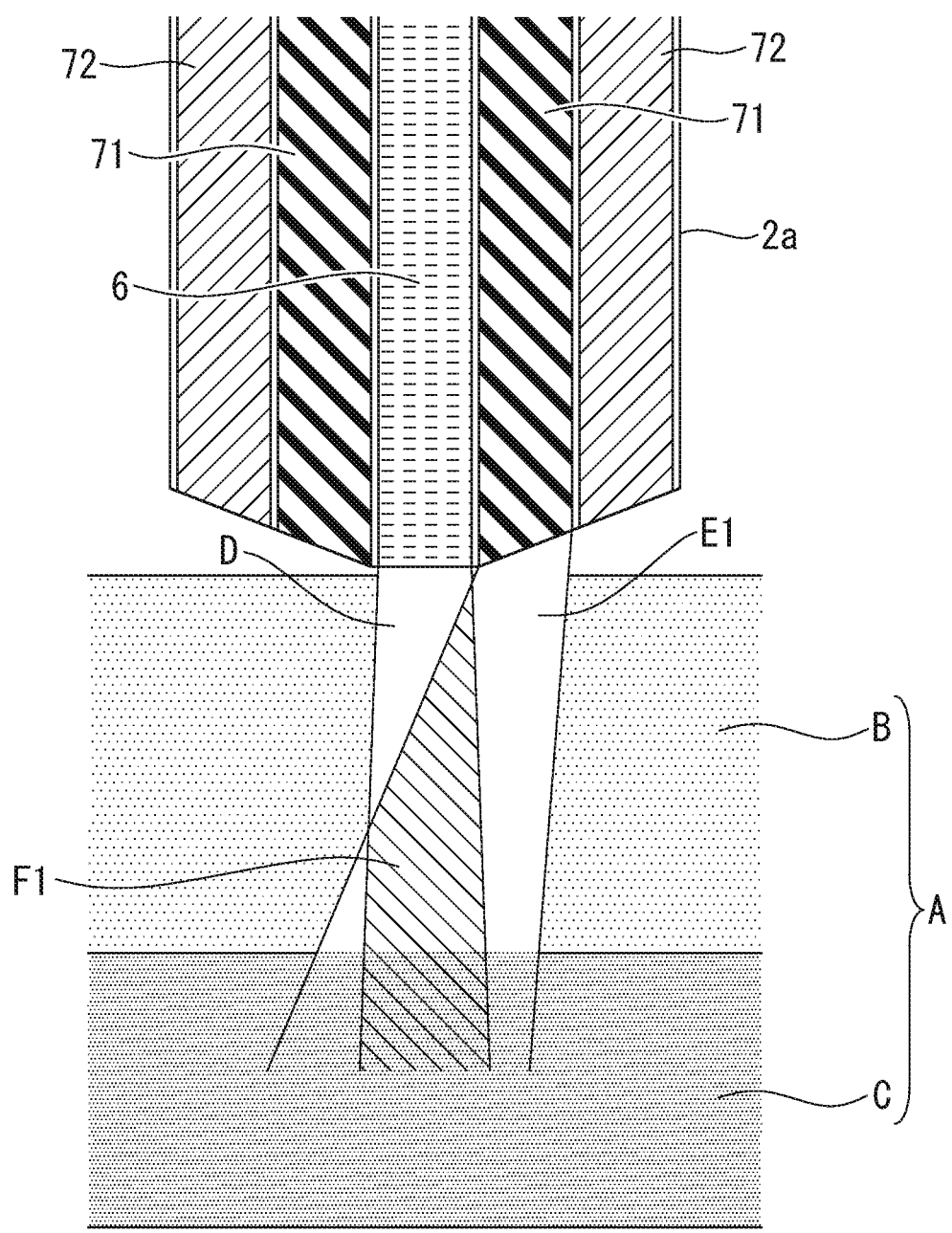
FIG. 5 is a diagram for illustrating the positional relationship between an illumination region of laser light emitted from an illuminating fiber and a first light-collecting region from which the scattered light is collected by a first light-collecting fiber.
Figure 6:
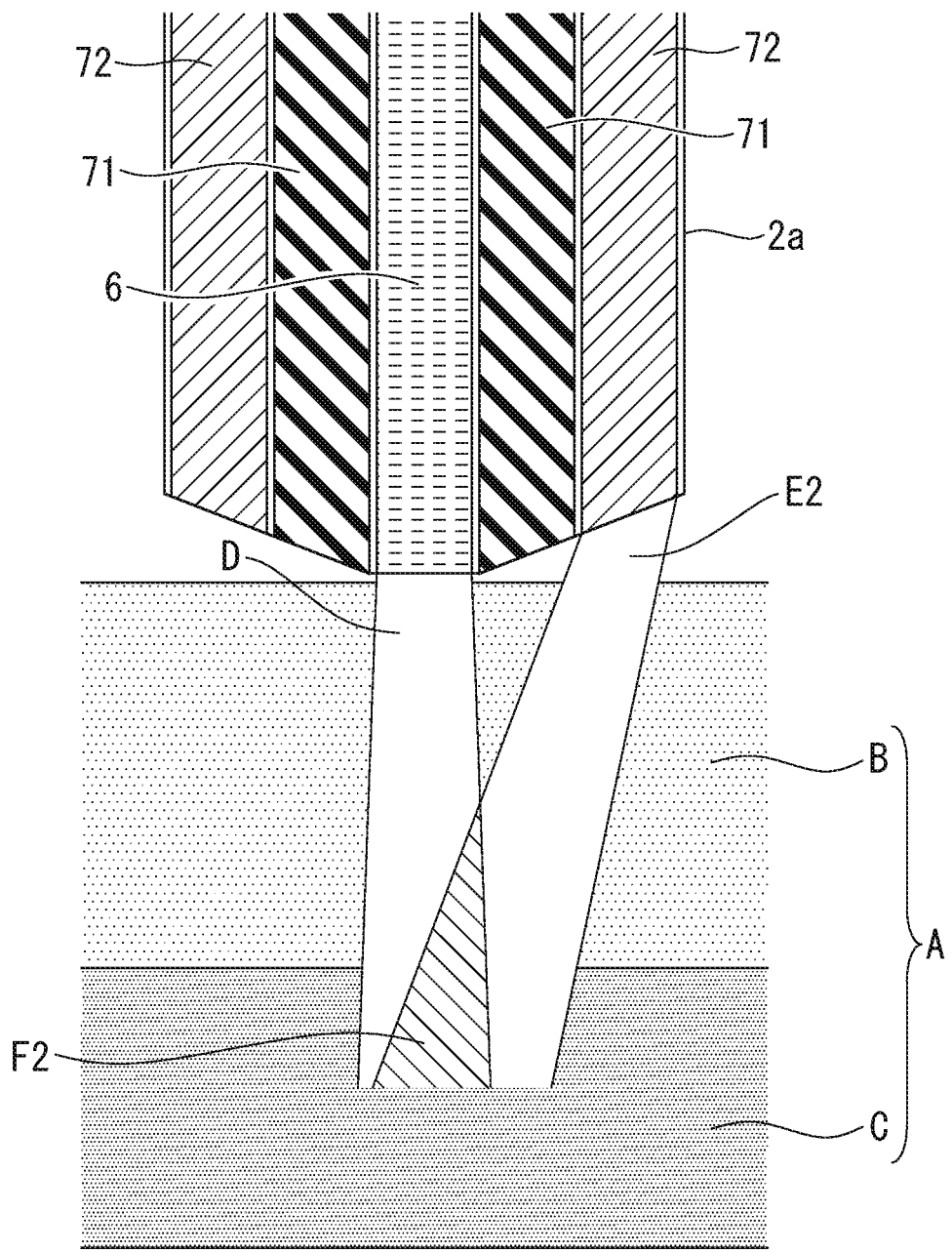
FIG. 6 is a diagram for illustrating the positional relationship between an illumination region of laser light emitted from an illuminating fiber and a second light-collecting region from which the scattered light is collected by a second light-collecting fiber.

On the other hand, as shown in FIGS. 3 and 4, the distal end surfaces of the light-collecting fibers 71 and 72 are tilted by a prescribed angle δ relative to a plane orthogonal to the longitudinal axis of the probe head 2a, i.e., the longitudinal axis parallel to the illuminating fiber 6 and the light-collecting fibers 71 and 72, thus orienting the distal end surfaces of the light-collecting fibers 71 and 72 obliquely outward. By doing so, as shown in FIGS. 5 and 6, the light-collecting fibers 71 and 72 collect light that is incident thereon from the illuminating fiber 6 side along directions oblique relative to the respective longitudinal axes thereof. This allows the volumes of areas F1 and F2 (examination areas), which are overlaps of light-collecting regions E1 and E2 (from which light is collected by the light-collecting fibers 71 and 72) and the illumination region D, to increase, compared with a case where the distal end surfaces of the light-collecting fibers 71 and 72 are formed so as to be orthogonal to the long axis of the probe head 2a. The amounts of Raman scattered light received by the light-collecting fibers 71 and 72 become larger as the volumes of the examination areas F1 and F2 increase, and hence, Raman scattered light generated in the proximity of the surface layer of the epiphysis A can be effectively collected by tilting the distal end surfaces of the light-collecting fibers 71 and 72, thereby making it possible to acquire a Raman spectrum of the epiphysis A with a high signal-to-noise ratio.

The prescribed angle δ is an angle determined depending on the magnitudes of the numerical apertures NA of the light-collecting fibers 71 and 72, and the smaller the numerical apertures NA of the light-collecting fibers 71 and 72, the larger the prescribed angle δ that can be set, thereby making it possible to collect Raman scattered light emitted from a region closer to the surface layer in the epiphysis A. For example, if the core diameter of the illuminating fiber 6 is 200 pm, the numerical aperture NA of the illuminating fiber 6 is 0.22, the core diameters of the light-collecting fibers 71 and 72 are 200 μm, and the numerical apertures NA of the light-collecting fibers 71 and 72 are 0.15, then a Raman spectrum originating from cartilage tissue B, which is, in the epiphysis A, tissue having a thickness from the surface of about 1 to 2 mm, can be selectively observed by setting the prescribed angle δ to a prescribed angle within the range from 30° to 37°. In addition, a Raman spectrum originating from even thinner cartilage tissue can be selectively observed by further reducing the core diameters of the illuminating fiber 6 and the light-collecting fibers 71 and 72.

In addition, a window material formed of synthetic quartz or sapphire may be disposed at the distal end surface of the probe head 2a so as to come into contact with the cross section (distal end surface) of the illuminating fiber 6, thereby providing an air gap between this window material and the distal end surfaces of the light-collecting fibers 71 and 72 forming the angle δ relative to a plane including this window material. If the light-collecting fibers 71 and 72 are immersed in a perfusate when measuring an epiphysis, the overlaps of the light-collecting regions E1 and E2 and the illumination region D become smaller because the difference in refractive index between the constituent materials of the light-collecting fibers 71 and 72 and water becomes smaller than the difference in refractive index between those constituent materials and air, and thus this is disadvantageous in observing the proximity of the surface layer of the epiphysis A. To overcome this problem, the overlaps of the light-collecting regions E1 and E2 and the illumination region D are maintained to be large by providing the air gap as described above, affording an advantage in that it is possible to selectively observe the cartilage tissue B in the proximity of the surface layer of the epiphysis A even in a water-immersion environment.

Here, because the first light-collecting fibers 71 are located closer to the illuminating fiber 6 than the second light-collecting fibers 72 are, the first examination area F1, which is the overlap of the first light-collecting region E1 and the illumination region D, becomes closer to the distal end portion of the probe head 2a than the second examination area F2, which is the overlap of the second light-collecting region E2 and the illumination region D, is. Therefore, the first light-collecting fibers 71 collect Raman scattered light from a relatively shallow position in the epiphysis A, and the second light-collecting fibers 72 collects Raman scattered light from a relatively deep position in the epiphysis A. In other words, Raman scattered light collected by the first light-collecting fibers 71 contains more Raman scattered light from the cartilage tissue B covering the surface layer region of the epiphysis A, compared with Raman scattered light collected by the second light-collecting fibers 72.

Figure 7:
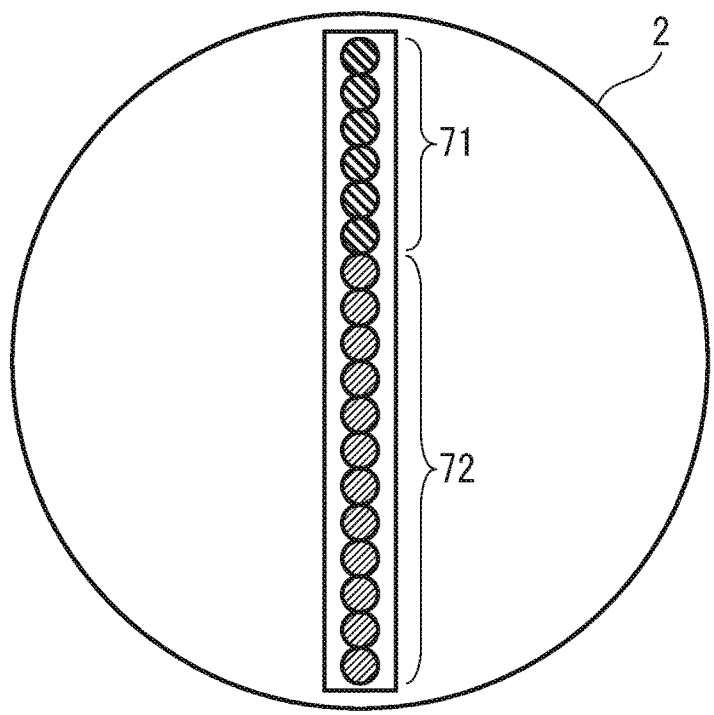
FIG. 7 is a transverse sectional view of the basal end portion of the optical probe in FIG. 1.
Figure 8:
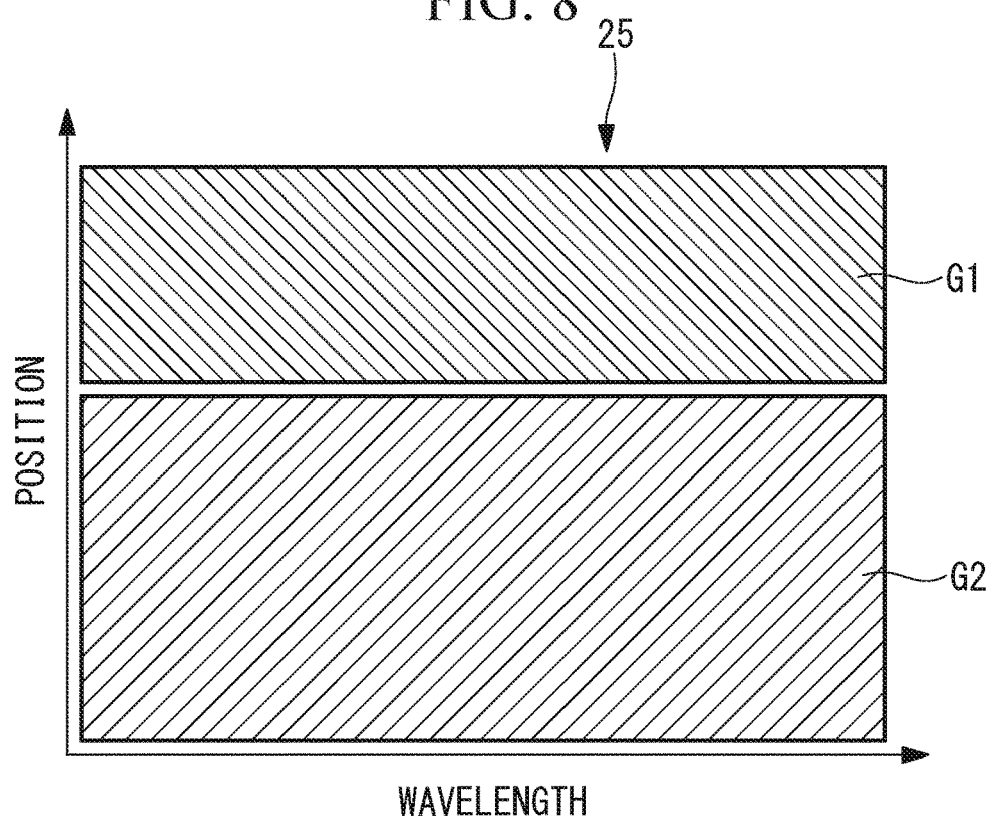
FIG. 8 is a diagram schematically depicting an image of a first Raman spectrum and a second Raman spectrum that is formed on a light-receiving surface of a photodetector in FIG. 1.

FIG. 7 is a transverse sectional view of the basal end portion of the optical probe 2. As shown in FIG. 7, at the basal end portion of the optical probe 2, the first light-collecting fibers 71 and the second light-collecting fibers 72 are arranged in a row so that the first light-collecting fibers 71 are aggregated on one side and the second light-collecting fibers 72 are aggregated on the other side. Therefore, as shown in FIG. 8, an image of Raman scattered light emitted from the first light-collecting fibers 71 is re-formed in a first light receiving region G1 on a light-receiving surface 25, and an image of Raman scattered light emitted from the second light-collecting fibers 72 is re-formed in a second light receiving region G2, which is different from the first light receiving region G1, on the light-receiving surface 25. By doing so, a first Raman spectrum of the first examination area F1 and a second Raman spectrum of the second examination area F2 are acquired in a manner separated from each other.

Figure 9:
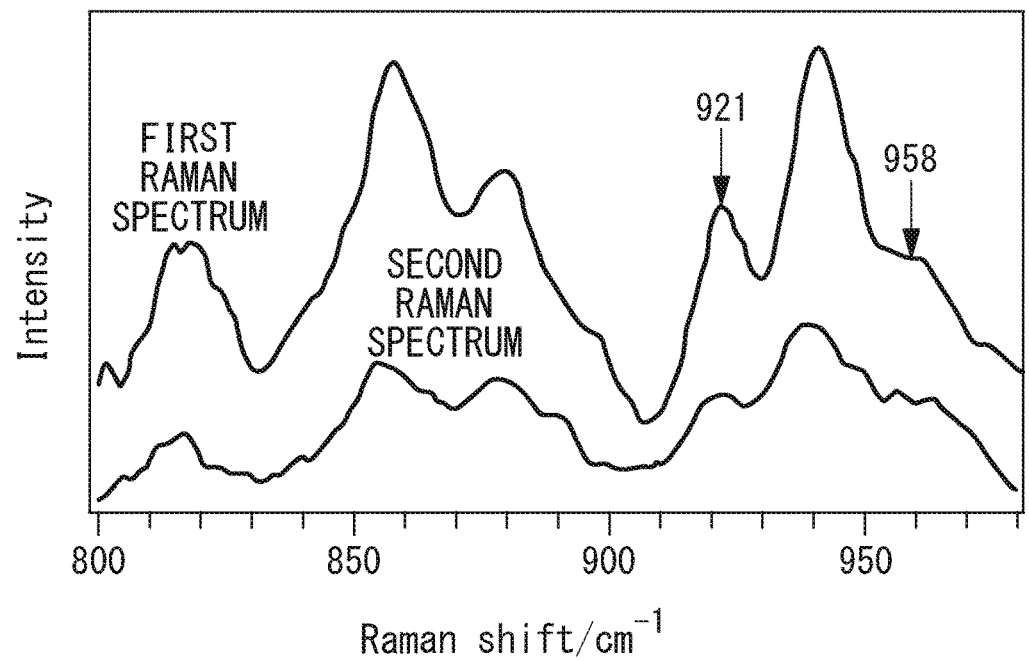
FIG. 9 is one example of a first Raman spectrum and a second Raman spectrum obtained from an epiphysis having thick cartilage tissue.
Figure 10:
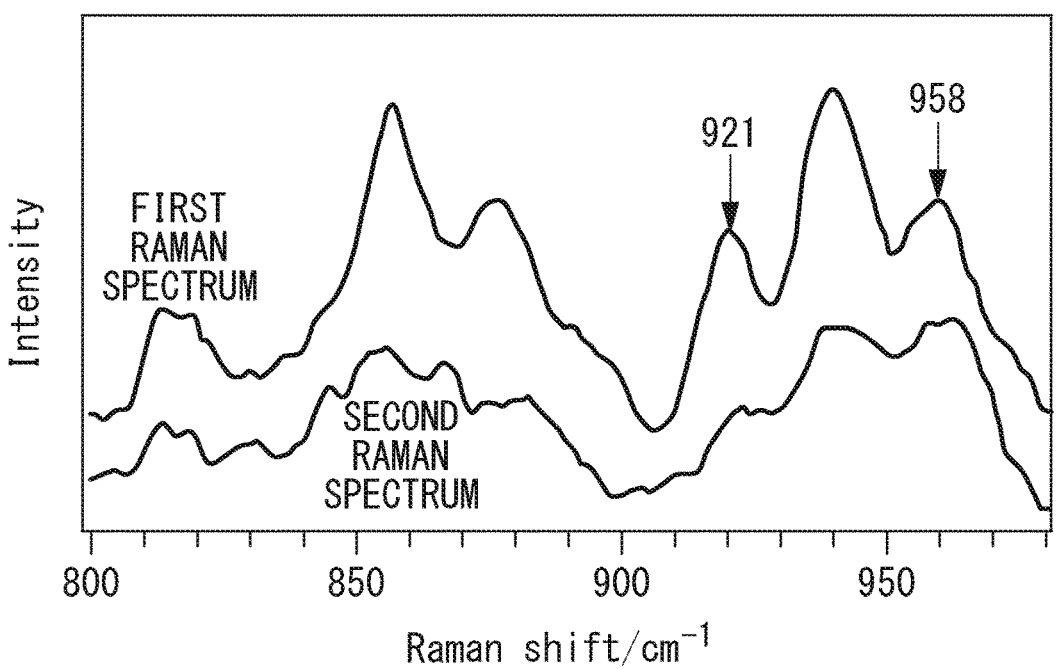
FIG. 10 is one example of a first Raman spectrum and a second Raman spectrum obtained from an epiphysis having thin cartilage tissue.

FIG. 9 shows portions of the first Raman spectrum and the second Raman spectrum obtained from the epiphysis A in which the cartilage tissue B is sufficiently thick, and FIG. 10 shows portions of the first Raman spectrum and the second Raman spectrum obtained from the epiphysis A in which the cartilage tissue B is thin.

Principal components contained in the cartilage tissue B are water, collagen (type II collagen), proteoglycan, which is a complex of glycosaminoglycan (GAG) and protein, and cartilage cells. Principal components contained in subchondral bone tissue C are collagen (type I collagen), calcium phosphate (hydroxyapatite), and calcium carbonate. In each of the Raman spectra in FIGS. 9 and 10, the Raman band having a peak in the proximity of 921 $cm^{-1}$ originates from proline, which is an amino acid contained in type II collagen in the cartilage tissue. Also, the Raman band having a peak in the proximity of 958 $cm^{-1}$ is a band formed as a result of a Raman band of type II collagen in the cartilage tissue being superimposed on a Raman band of a phosphate group in calcium phosphate (hydroxyapatite) in the subchondral bone tissue.

Focusing on the intensities of the two Raman bands at 921 $cm^{-1}$ and 958 $cm^{-1}$ in each of the spectra shown in FIGS. 9 and 10, the intensities of the Raman band at 921 $cm^{-1}$ and the Raman band at 958 $cm^{-1}$ are almost the same in each of the first Raman spectrum and the second Raman spectrum in FIG. 9. On the other hand, in the first Raman spectrum and the second Raman spectrum in FIG. 10, the Raman band intensity at 958 $cm^{-1}$ is larger than the Raman band intensity at 921 $cm^{-1}$ in the second Raman spectrum. This means that the second Raman spectrum in FIG. 10 contains a greater contribution made by the Raman spectrum originating from hydroxyapatite, which is a component of the subchondral bone tissue, compared with the second Raman spectrum in FIG. 9. In this manner, it is understood that most of the signals contained in the first and second Raman spectra in FIG. 9 are signals from the cartilage tissue B, whereas the first Raman spectrum and the second Raman spectrum in FIG. 10 contain not only signals originating from components of the cartilage tissue B but also signals originating from components of the subchondral bone tissue C.

As shown in FIG. 1, the cartilage-tissue analysis device 100 further includes: a control unit 8; a memory unit 9; a calculation unit (intensity-ratio calculation unit, evaluation unit) 10; and a display unit 11.

The control unit 8 controls the irradiation intensity and irradiation timing of the laser light by controlling the output intensity and the output timing of the laser light emitted from the laser light source 1. In addition, the control unit 8 controls the center wavelength of the spectrometer 3, as well as conditions for detecting light (e.g., exposure time and gain) by means of the photodetector 5.

The memory unit 9 stores data on the first and second Raman spectra acquired by the photodetector 5 and calculation results (described later) from the calculation unit 10.

The display unit 11 displays Raman spectra stored in the memory unit 9 and calculation results from the calculation unit 10.

The calculation unit 10 reads out data on the first and second Raman spectra from the memory unit 9 and executes the following first and second processes for analyzing the first and second Raman spectra and evaluating the state of the cartilage tissue B contained in the epiphysis A.

In the first process, the calculation unit 10 selects, from among the first and second Raman spectra, a Raman spectrum corresponding to a Raman spectrum of the cartilage tissue B. More specifically, the calculation unit 10 calculates an intensity ratio between a Raman band originating from the cartilage tissue B and a Raman band originating from the subchondral bone tissue C in the first Raman spectrum (first band intensity ratio), as defined in the following expression:

Band intensity ratio=intensity of Raman band originating from cartilage tissue/intensity of Raman band originating from subchondral bone tissue In the same manner, the calculation unit 10 calculates an intensity ratio between a Raman band originating from the cartilage tissue B and a Raman band originating from the subchondral bone tissue C in the second Raman spectrum (second band intensity ratio).

The Raman band originating from the cartilage tissue B is a Raman band of, for example, type II collagen. For this purpose, the Raman band of amino acid (proline) at 921 $cm^{-1}$ or the Raman band of collagen polypeptide backbone at 815 $cm^{-1}$ can be used. The Raman band originating from the subchondral bone tissue C is, for example, the Raman band, at 958 $cm^{-1}$, of phosphoric acid ions contained in hydroxyapatite (HAP). The Raman band intensity may be represented as the peak value or the integrated intensity of the band.

Subsequently, the calculation unit 10 compares the first band intensity ratio and the second band intensity ratio with respective prescribed threshold values and selects, as the Raman spectrum of the cartilage tissue B, the Raman spectrum having a band intensity ratio greater than the prescribed threshold value.

Here, the relationship between the thickness of the cartilage tissue B and the Raman band intensity ratio, as well as the prescribed threshold values, will be described.

Figure 11A:
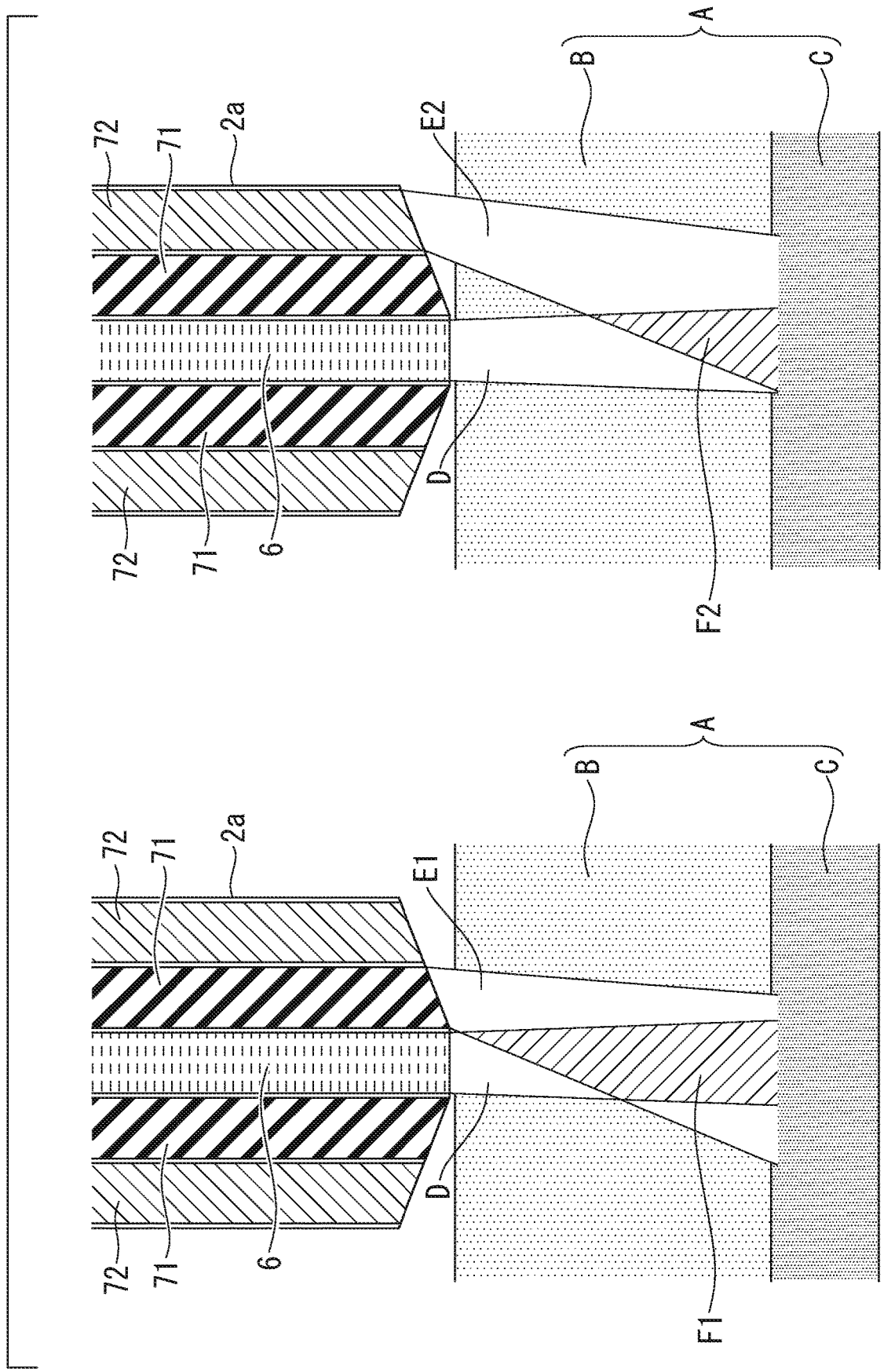
FIG. 11A is a diagram for illustrating positional relationships between cartilage tissue and examination areas in a case where the tissue thickness of the cartilage tissue is sufficiently thick for the examination areas.
Figure 11B:
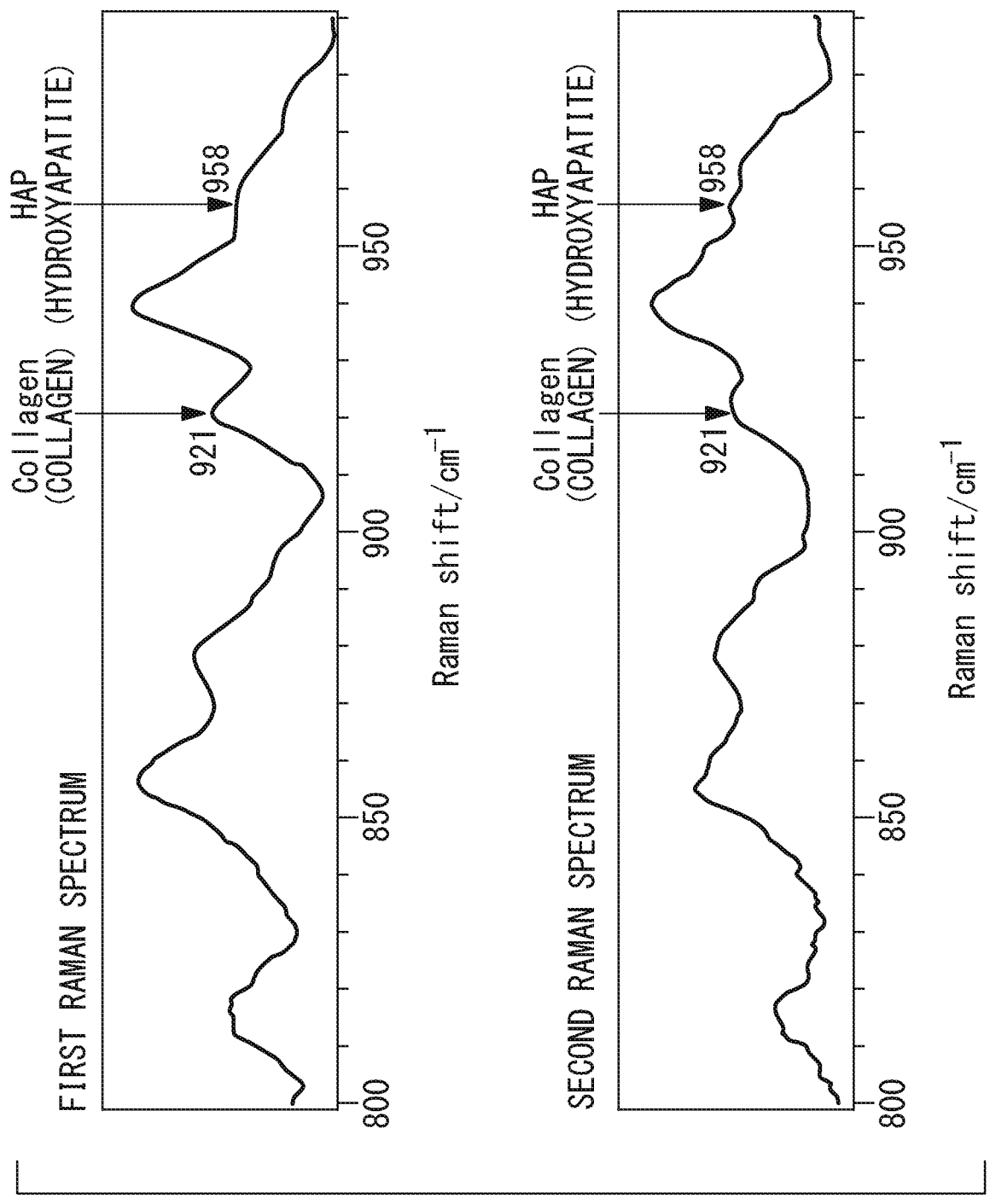
FIG. 11B is one example of a first Raman spectrum and a second Raman spectrum obtained from an epiphysis having sufficiently thick cartilage tissue for the examination areas.

FIG. 11A illustrates the relationship between: the examination area F1 and the examination area F2; and the epiphysis A in a case where the cartilage tissue B is thick enough to include the examination area F1 and examination area F2. In this case, as shown in FIG. 11B, the first Raman spectrum acquired with the light-collecting fibers 71 and the second Raman spectrum acquired with the light-collecting fibers 72 are mostly attributable to the Raman spectrum of the cartilage tissue B. At this time, the Raman band intensity of collagen having a peak at 921 $cm^{-1}$ and the Raman band intensity of hydroxyapatite (HAP) having a peak at 958 $cm^{-1}$ are substantially identical to each other.

Figure 12A:
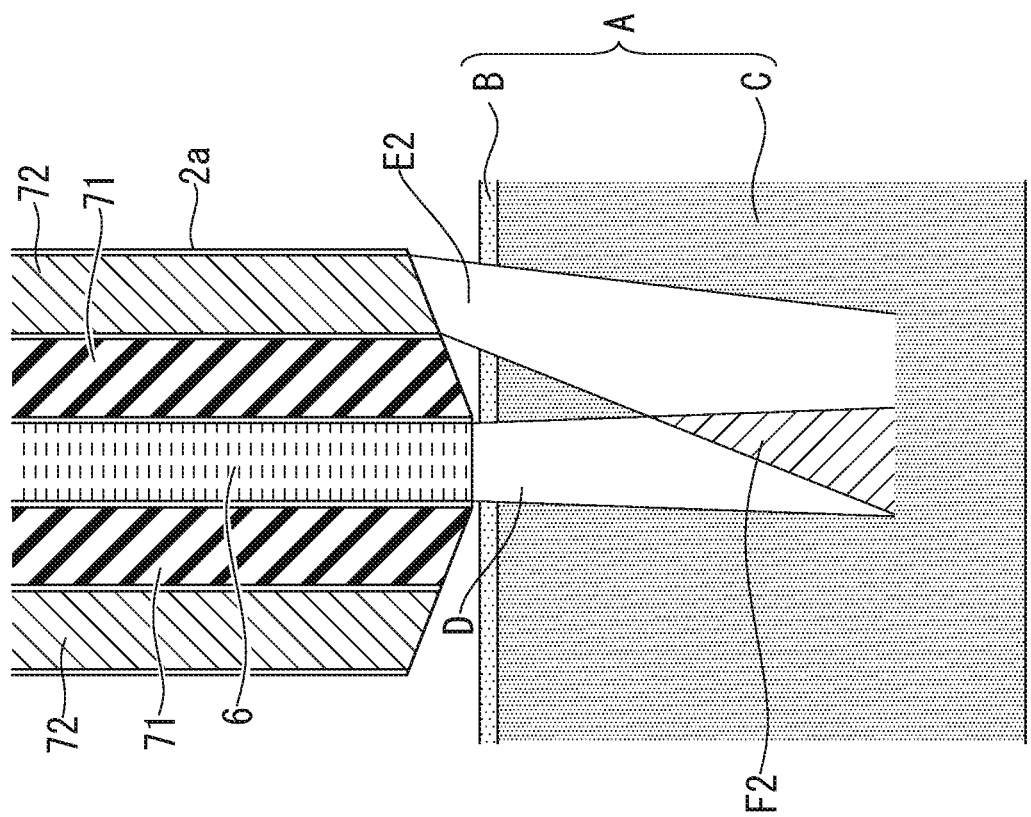
FIG. 12A is a diagram for illustrating positional relationships between cartilage tissue and examination areas in a case where the tissue thickness of the cartilage tissue is sufficiently thin for the examination areas.
Figure 12A:
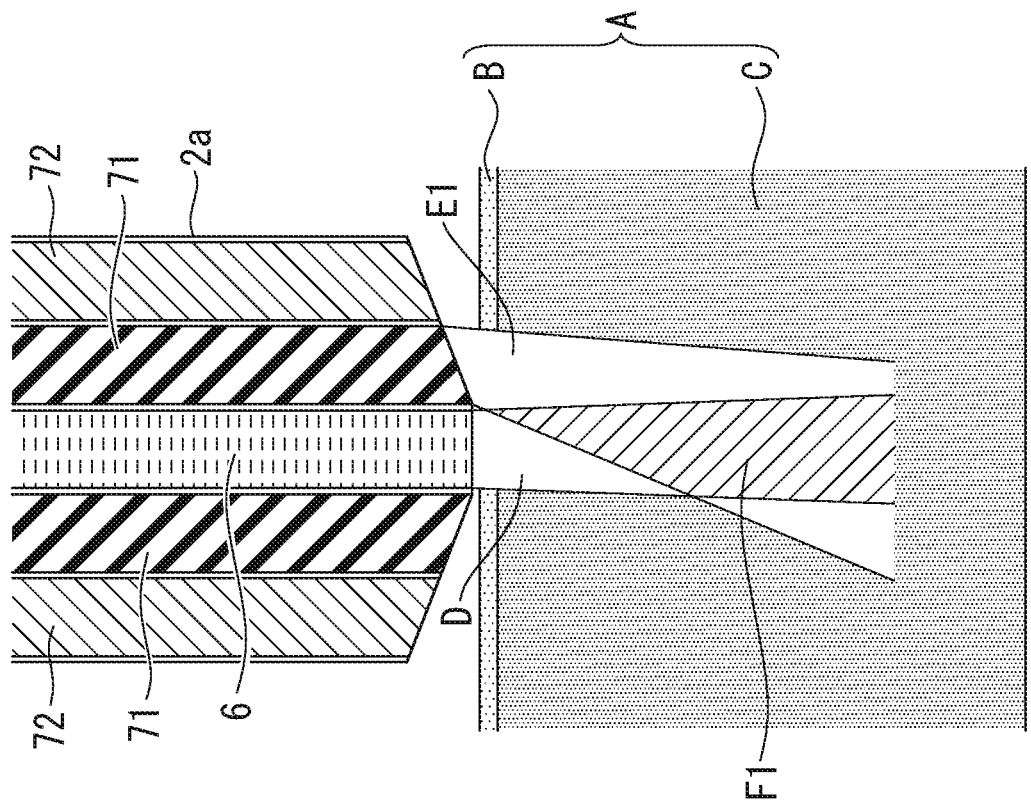
Figure 12B:
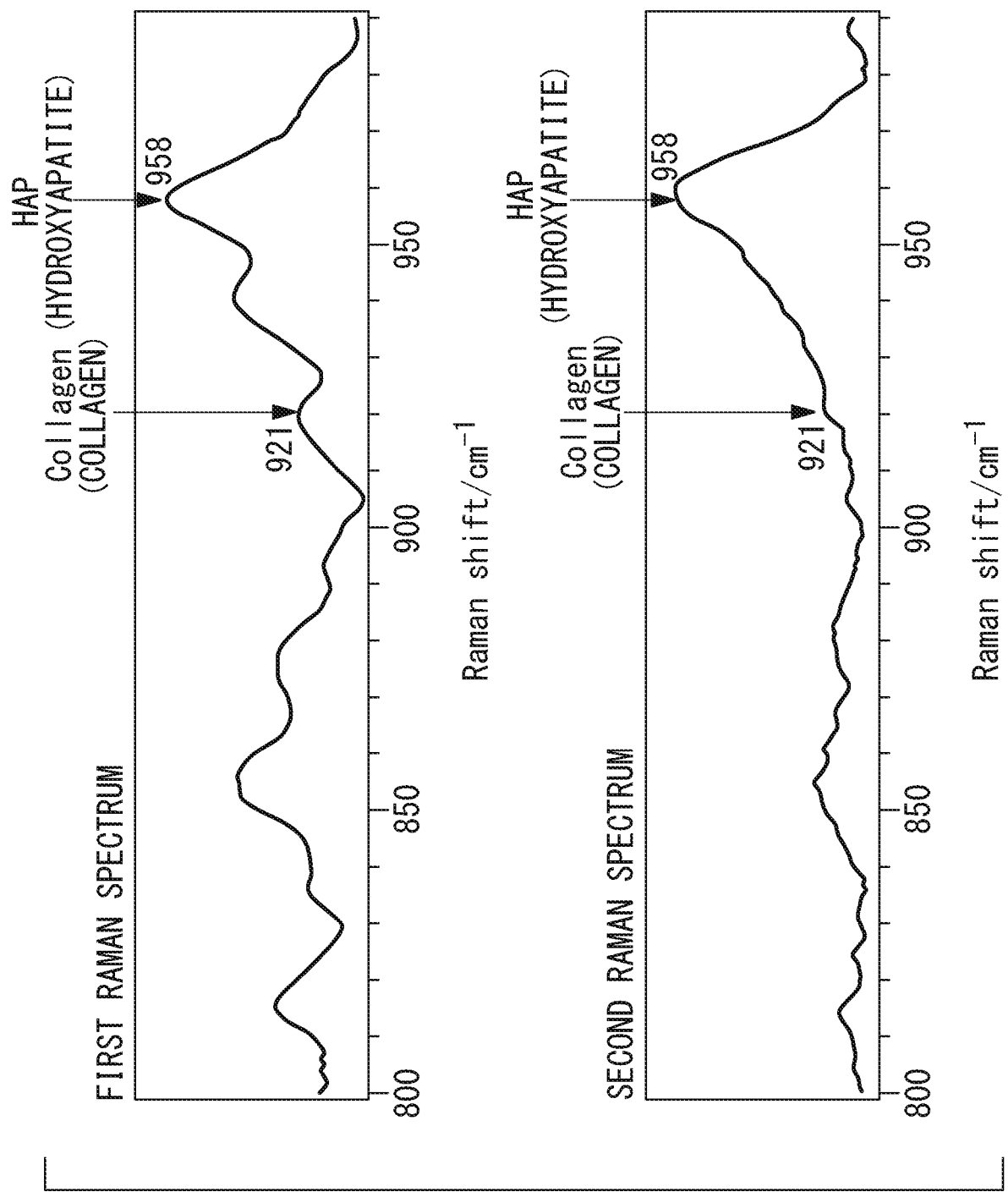
FIG. 12B is one example of a first Raman spectrum and a second Raman spectrum obtained from an epiphysis having sufficiently thin cartilage tissue for the examination areas.

FIG. 12A illustrates the relationship between: the examination area F1 and the examination area F2; and the epiphysis A in a case where the cartilage tissue B is so thin that the cartilage tissue B barely includes the examination area F1 and the examination area F2 or in a case where the cartilage tissue B is not present. In this case, the first Raman spectrum acquired with the light-collecting fibers 71 and the second Raman spectrum acquired with the light-collecting fibers 72 are mostly attributable to the Raman spectrum of the subchondral bone tissue C, as shown in FIG. 12B. The Raman band intensity of hydroxyapatite (HAP) having a peak at 958 $cm^{-1}$ in this case is 10 times or more the Raman band intensity of collagen having a peak at 921 $cm^{-1}$.

Figure 13B:
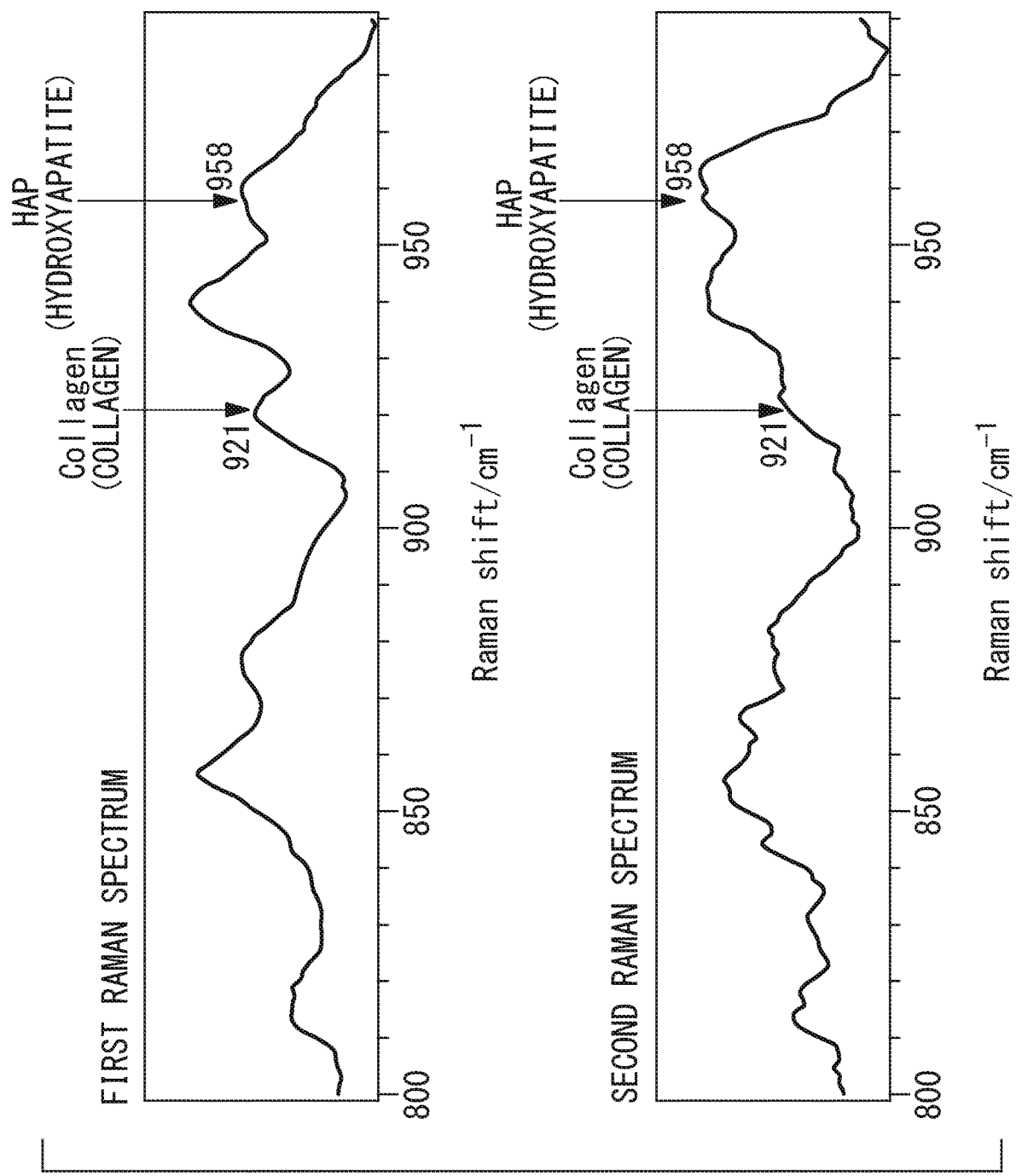
FIG. 13B is one example of a first Raman spectrum and a second Raman spectrum obtained from an epiphysis in which the cartilage tissue has a thickness as in the case of FIG. 13A for the examination areas.

FIG. 13A illustrates a case where the thickness of the cartilage tissue B is between the thickness in the case shown in FIG. 11A and the thickness in the case shown in FIG. 12A. In this case, as shown in FIG. 13B, the intensity ratio between the Raman band of collagen having a peak at 921 $cm^{-1}$ and the Raman band of hydroxyapatite (HAP) having a peak at 958 $cm^{-1}$ in each of the first Raman spectrum acquired with the light-collecting fibers 71 and the second Raman spectrum acquired with the light-collecting fibers 72 changes depending on the ratio between the cartilage tissue B and the subchondral bone tissue C contained in the examination area F1 and the examination area F2.

In this manner, the intensity ratio between the Raman band of collagen having a peak at 921 $cm^{-1}$ and the Raman band of hydroxyapatite having a peak at 958 $cm^{-1}$ differs according to the thickness of the cartilage tissue B in the epiphysis A and changes depending on the proportion of the contribution made by the cartilage tissue B to each of the first and second Raman spectra. Therefore, on the basis of these band intensity ratios, a Raman spectrum to which the subchondral bone tissue C makes a smaller contribution and to which the cartilage tissue B makes a greater contribution can be selected from among the first and second Raman spectra.

The prescribed threshold value serving as a reference for selecting the Raman spectrum of the cartilage tissue B is experimentally determined.

For example, when the band intensity ratios between the Raman bands at 921 $cm^{-1}$ and 958 $cm^{-1}$ were calculated by measuring Raman spectra of swine epiphyses (number of samples n=20) that have cartilage tissue sufficiently thick for the examination area F1, the band intensity ratios ranged from 0.80 to 1.25 inclusive. Therefore, the Raman spectrum of the cartilage tissue B can be selectively observed from the Raman spectrum of the epiphysis A by setting the prescribed threshold value to a value equal to or larger than the minimum value in the above-described range.

The prescribed threshold value is set to, for example, 0.8. In the case of the first and second Raman spectra shown in FIG. 9, the band intensity ratios are 1.15 and 1.0, respectively. Therefore, both the first and second Raman spectra are selected as Raman spectra of the cartilage tissue. In such a case, only the first Raman spectrum may be used as the Raman spectrum of the cartilage tissue B for the subsequent second process, or alternatively, the sum of the first Raman spectrum and the second Raman spectrum may be used for the subsequent second process. In the case of the first and second Raman spectra shown in FIG. 10, the band intensity ratios are 0.95 and 0.56, respectively. Therefore, only the first Raman spectrum is selected as the Raman spectrum of the cartilage tissue B.

Next, in the second process, the calculation unit 10 calculates the amount of glycosaminoglycan (GAG) contained in the cartilage tissue B by analyzing the selected Raman spectrum of the cartilage tissue B and evaluates the state of the cartilage tissue B on the basis of the calculated amount of glycosaminoglycan (GAG). More specifically, the calculation unit 10 calculates the intensity of a Raman band of collagen and the intensity of a Raman band of glycosaminoglycan (GAG) from the Raman spectrum of the cartilage tissue B. As the Raman band of collagen, for example, the Raman band of a proline residue at 921 $cm^{-1}$ or the Raman band of collagen at 815 $cm^{-1}$ is selected. As the Raman band of glycosaminoglycan (GAG), for example, the Raman band of a sulfated glycosaminoglycan (GAG) sulfate group at 1063 $cm^{-1}$ or the Raman band at 1380 $cm^{-1}$ is selected. Each of the Raman band intensities may be represented as the peak value or the integrated intensity of the band.

Figure 14:
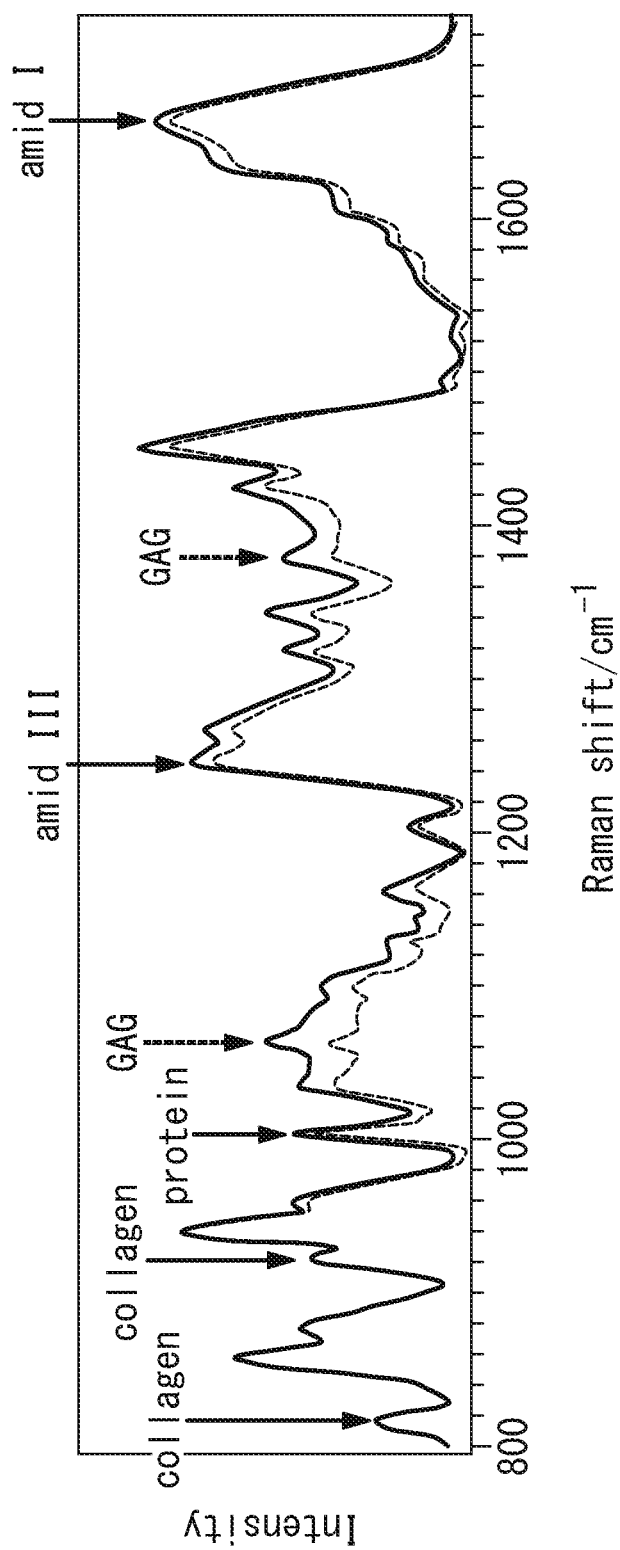
FIG. 14 is a diagram depicting a Raman spectrum of normal cartilage tissue (solid line) and a Raman spectrum of lesional cartilage tissue (broken line) from which sulfated glycosaminoglycan (GAG) is deleted.

FIG. 14 shows one example of the Raman spectrum of the cartilage tissue B that is selected in the first process after a Raman spectrum of the epiphysis A has been acquired in the cartilage-tissue analysis device 100 shown in FIG. 1. In FIG. 14, the solid line indicates the Raman spectrum of the cartilage tissue B in a normal epiphysis A, and the broken line indicates the Raman spectrum of the cartilage tissue B in the epiphysis A of a lesion model in which glycosaminoglycan (GAG) has been partially deleted by immersing a normal epiphysis A in a proteoglycan-degrading enzyme (trypsin). When the two Raman spectra are compared, the intensities of the Raman bands of collagen at 921 $cm^{-1}$ do not differ between the two Raman spectra. On the other hand, the intensities of the Raman bands of sulfated glycosaminoglycan (GAG) in the proximity of 1063 $cm^{-1}$ and in the proximity of 1380 $cm^{-1}$ are smaller in the Raman spectrum of the cartilage tissue in which glycosaminoglycan (GAG) has been deleted than those in the Raman spectrum of the normal epiphysis.

Subsequently, the calculation unit 10 calculates the intensity ratio between a Raman band of sulfated glycosaminoglycan (GAG) and a Raman band of collagen (intensity of Raman band of GAG/intensity of Raman band of collagen), GAG/Col. As the Raman band of sulfated glycosaminoglycan, the Raman band having an intensity peak in the proximity of 1063 $cm^{-1}$ or in the proximity of 1380 $cm^{-1}$ can be used. As the Raman band of collagen, the Raman band having an intensity peak in the proximity of 921 $cm^{-1}$ or in the proximity of 940 $cm^{-1}$ can be used.

Figure 15A:
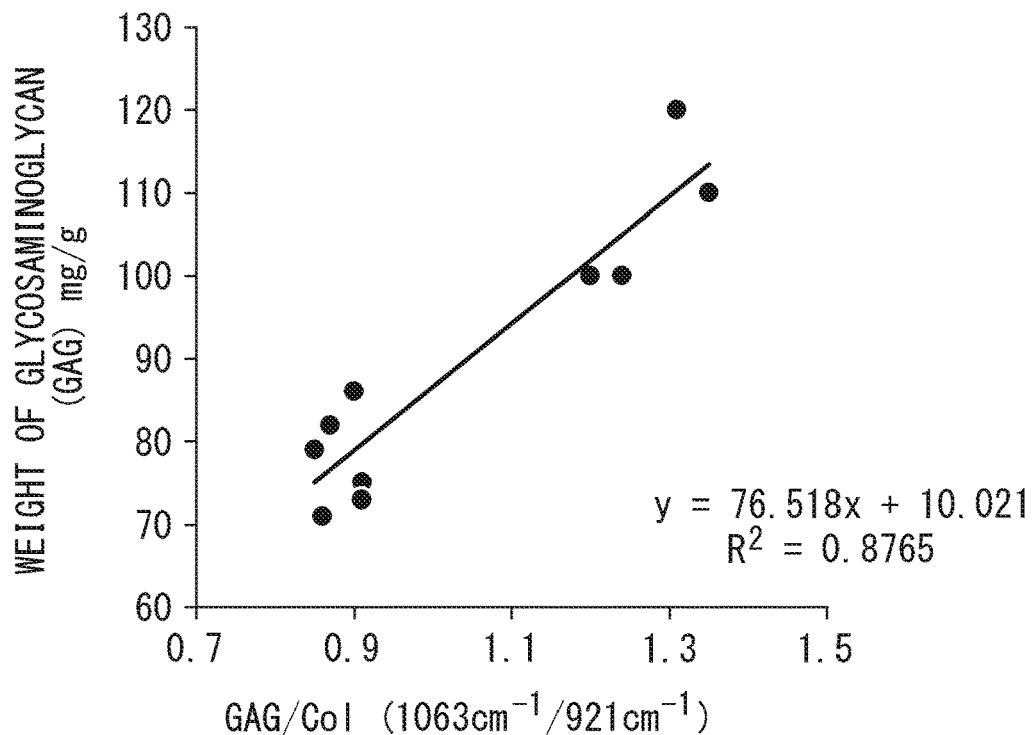
FIG. 15A is a graph showing the correlation between: the intensity ratio between Raman bands of sulfated glycosaminoglycan (GAG) (1063 cm$^{-1}$) and collagen; and the amount of sulfated glycosaminoglycan (GAG) in the cartilage tissue.
Figure 15B:
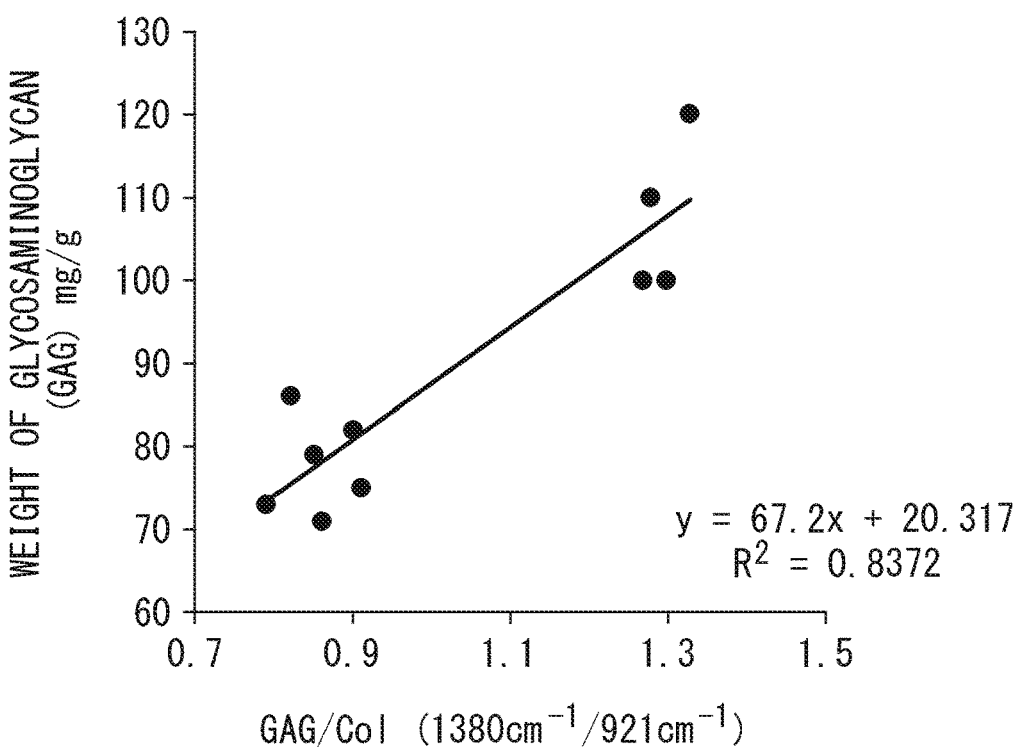
FIG. 15B is a graph showing the correlation between: the intensity ratio between Raman bands of sulfated glycosaminoglycan (GAG) (1380 cm$^{-1}$) and collagen; and the amount of sulfated glycosaminoglycan (GAG) in the cartilage tissue.

FIGS. 15A and 15B show correlations between: the intensity ratio between the Raman bands, GAG/Col; and the weight of sulfated glycosaminoglycan (GAG) per unit wet weight of the cartilage tissue obtained through biochemical analysis. Whichever of the Raman bands in the proximity of 1063 cm$^{-1}$ and in the proximity of 1380 cm$^{-1}$ was used as the Raman band of sulfated glycosaminoglycan (GAG), the intensity ratio GAG/Col exhibited a correlation having a correlation coefficient of as high as 0.9 or more with respect to the amount of glycosaminoglycan (GAG) in the cartilage tissue. It is known that, compared with normal cartilage tissue, the amount of GAG, such as chondroitin sulfate, decreases in regenerated cartilage that is still in the process of regeneration and that has not matured into hyaline cartilage, as well as in fibrous cartilage and osteoarthritis cartilage tissue. The calculation unit 10 estimates the amount of GAG in the cartilage tissue B on the basis of the intensity ratio between the Raman bands, GAG/Col, and evaluates the state of the cartilage tissue B, such as regenerated cartilage or osteoarthritis cartilage tissue.

The analysis results, such as the amount of GAG and the evaluation result, obtained by the calculation unit 10 are stored in the memory unit 9 and displayed on the display unit 11.

Next, the operation of the cartilage-tissue analysis device 100 with the above-described configuration will now be described.

Figure 16:
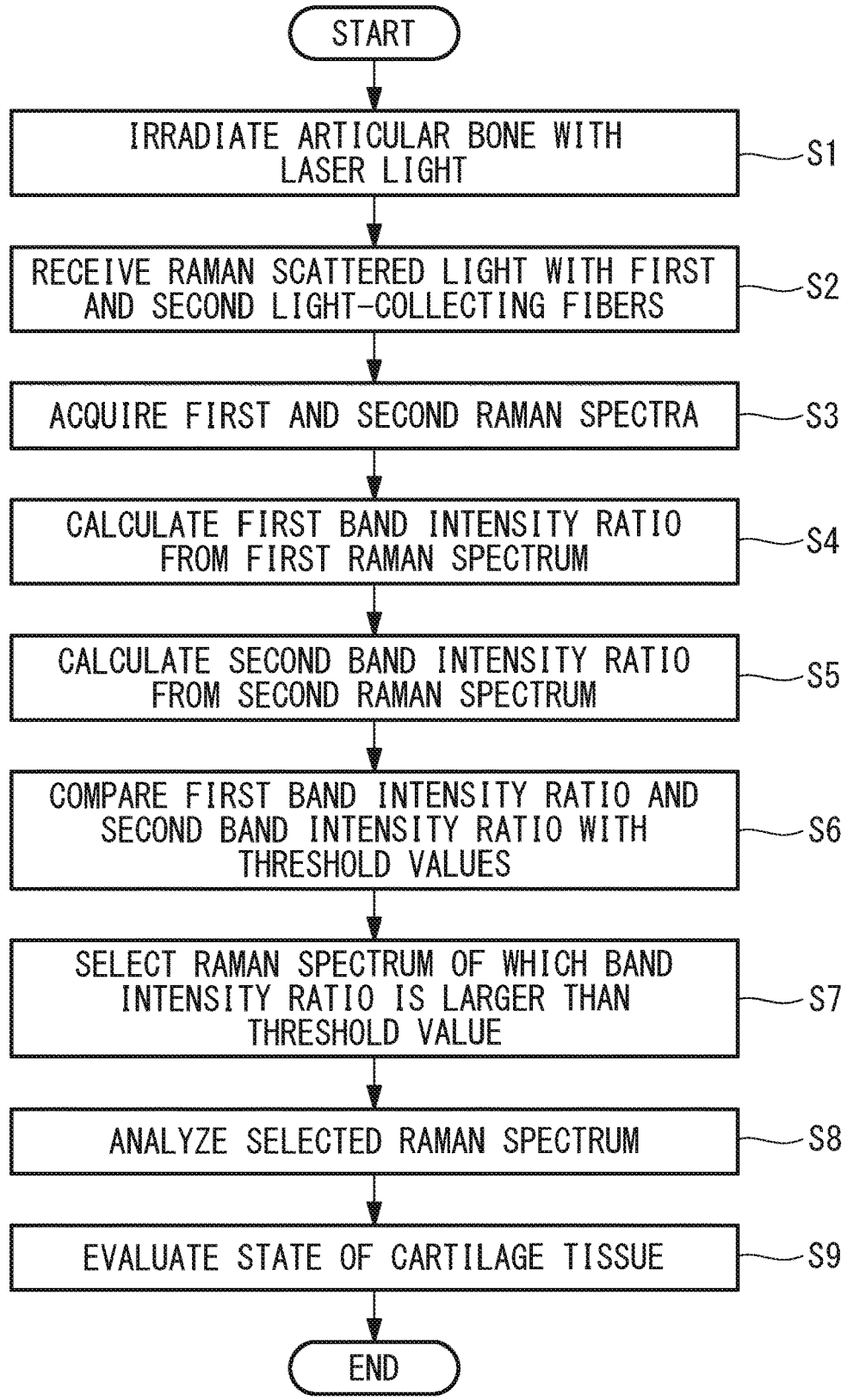
FIG. 16 is a flowchart for illustrating the operation of the cartilage-tissue analysis device in FIG. 1.

As shown in FIG. 16, laser light output from the laser light source 1 is guided by the illuminating fiber 6 of the optical probe 2 and is radiated from the probe head 2a onto the epiphysis A (step S1). Raman scattered light originating from components of the epiphysis A is generated in the illumination region D of the epiphysis A as a result of being irradiated with the laser light, and the Raman scattered light (inelastic scattered light) and scattered light of the laser light (elastic scattered light) are diffusely reflected from the epiphysis A. Of the scattered light diffusely reflected from the epiphysis A, scattered light from the first examination area F1 is received by the first light-collecting fibers 71, and scattered light from the second examination area F2 is received by the second light-collecting fibers 72 (step S2).

The scattered light received by the first light-collecting fibers 71 and the second light-collecting fibers 72 are guided to the spectrometer 3 via the coupling optical system 4, are spatially dispersed by the spectrometer 3 for each wavelength, and are detected by the photodetector 5. By doing so, the first Raman spectrum of the first examination area F1 and the second Raman spectrum of the second examination area F2 are acquired (step S3). The acquired Raman spectra are stored in the memory unit 9 and transmitted to the calculation unit 10.

Next, in the calculation unit 10, the first band intensity ratio is calculated from the intensity of a Raman band of the cartilage tissue B and the intensity of a Raman band of the subchondral bone tissue C in the first Raman spectrum (step S4). In the same manner, the second band intensity ratio is calculated from the intensity of the Raman band of the cartilage tissue B and the intensity of the Raman band of the subchondral bone tissue C in the second Raman spectrum (step S5). Next, from among the first and second Raman spectra, a Raman spectrum that exhibits a band intensity ratio greater than a prescribed threshold value is selected as the Raman spectrum of the cartilage tissue B (steps S6 and S7).

Next, in the calculation unit 10, the intensity ratio between Raman bands of glycosaminoglycan (GAG) and collagen, GAG/Col, in the selected Raman spectrum of the cartilage tissue B is calculated (step S8), and the state of the cartilage tissue B is evaluated on the basis of the calculated intensity ratio GAG/Col (step S9). The evaluation result is displayed on the display unit 11. The evaluation result of the cartilage tissue B displayed on the display unit 11 is, for example, an estimated amount of glycosaminoglycan (GAG) in the cartilage tissue B. Alternatively, the evaluation result may be a classification index indicating the state of the cartilage tissue B, where the classification index is graded so as to correlate with the estimated amount of glycosaminoglycan (GAG).

In this manner, according to this embodiment, two Raman spectra of the examination areas F1 and F2 at different depths in the epiphysis A are acquired by both the first light-collecting fibers 71 and the second light-collecting fibers 72, the distal end surfaces of which are disposed at mutually different distances from the distal end surface of the illuminating fiber 6. Also, by selecting the Raman spectrum of the cartilage tissue B on the basis of the intensity ratio between the Raman band originating from the cartilage tissue B and the Raman band originating from the subchondral bone tissue C that is calculated from each of the first and second Raman spectra, the Raman spectrum of the cartilage tissue B from which the influence of the signals originating from the subchondral bone tissue C has been excluded as much as possible can be used for evaluation. This affords an advantage in that it is possible to evaluate, with high accuracy, the state of regenerated cartilage in the process of regeneration in the cartilage tissue B that is present in the surface layer of the epiphysis A and the state of the cartilage tissue B, for example, in early-stage osteoarthritis, which develops an abnormality only in the cartilage tissue B that is present in the surface layer of the epiphysis A.

Although, in this embodiment, the plurality of first light-collecting fibers 71 and the plurality of second light-collecting fibers 72 are arranged so as to form concentric circles, the numbers of first light-collecting fibers 71 and second light-collecting fibers 72 and the arrangement thereof are not limited to those in this embodiment.

Figure 17A:
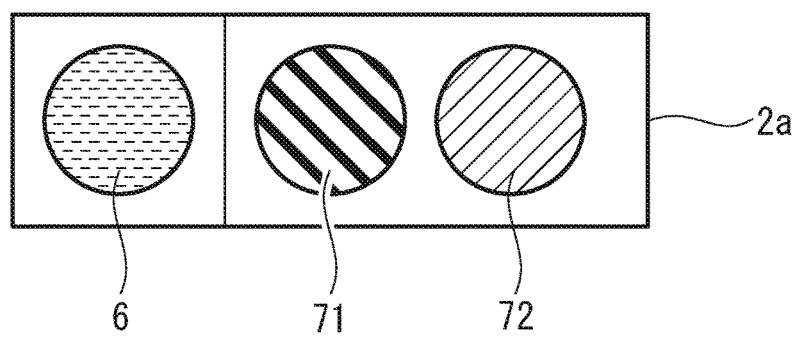
FIG. 17A is a transverse sectional view of a modification of the distal end portion of the optical probe in FIG. 2.
Figure 17B:
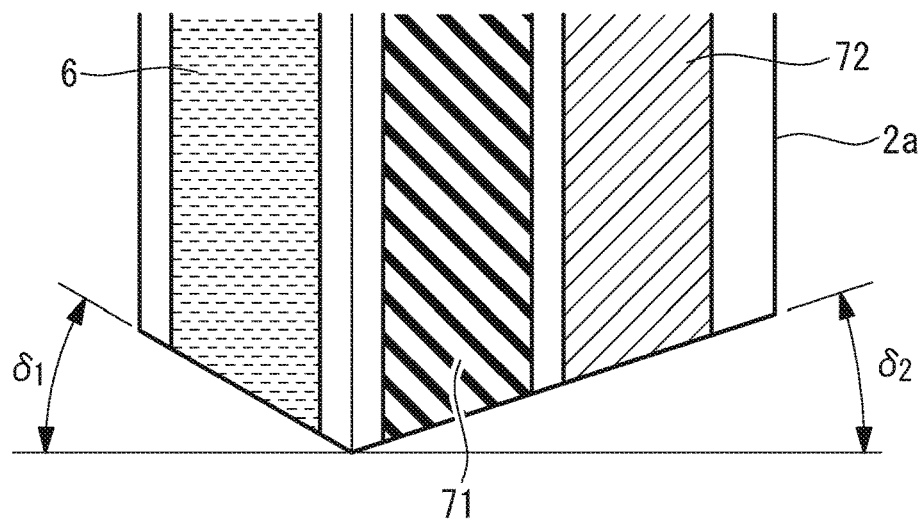
FIG. 17B is a longitudinal sectional view of the optical probe in FIG. 17A.
Figure 17C:
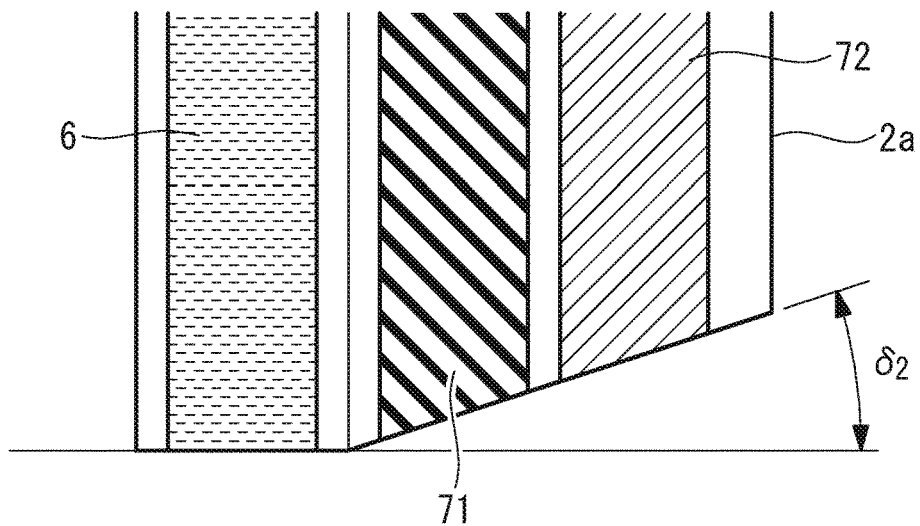
FIG. 17C is a longitudinal sectional view of another example of the optical probe in FIG. 17A.

As shown in, for example, FIGS. 17A to 17C, only one first light-collecting fiber 71 and only one second light-collecting fiber 72 may be arranged, and the illuminating fiber 6, the first light-collecting fiber 71, and the second light-collecting fibers 72 may be arranged in a row in the radial direction. Also in this case, the optical fibers 6, 71, and 72 are arranged such that the distance from the distal end surface of the illuminating fiber 6 to the distal end surface of the first light-collecting fiber 71 differs from the distance from the distal end surface of the illuminating fiber 6 to the distal end surface of the second light-collecting fiber 72.

As shown in FIG. 17C, the distal end surfaces of the light-collecting fibers 71 and 72 are tilted by a prescribed angle 52 relative to a plane orthogonal to the long axis direction of the probe head 2a. Alternatively, as shown in FIG. 17B, not only are the distal end surfaces of the light-collecting fibers 71 and 72 tilted by the prescribed angle δ2 relative to a plane orthogonal to the long axis direction of the probe head 2a, but also the distal end surface of the illuminating fiber 6 may be tilted by a prescribed angle δ1 relative to a plane orthogonal to the long axis direction of the probe head 2a. By doing so, the examination areas F1 and F2, which are overlaps of the illumination region D formed by the illuminating fiber 6 and the light-collecting regions E1 and E2 formed by the light-collecting fibers 71 and 72, are formed at positions closer to the distal end of the probe head 2a. Therefore, this structure is more effective than the structure shown in FIG. 17C when the cartilage tissue B that is present in the surface layer of the epiphysis A is observed.

Although Raman bands of collagen and HAP are used to calculate the first and second band intensity ratios in this embodiment, a Raman band of glycosaminoglycan (GAG), instead of collagen, may be used as the Raman band originating from the cartilage tissue B since glycosaminoglycan (GAG) is contained only in the cartilage tissue B and is not contained in the subchondral bone tissue C.

The intensity ratio between the Raman bands of glycosaminoglycan (GAG) and hydroxyapatite (HAP) also reflects the proportion of the contribution made by the Raman spectrum of the cartilage tissue B to each of the first and second Raman spectra. Therefore, the Raman spectrum of the cartilage tissue B can be selected on the basis of this intensity ratio.

The intensity ratio between the Raman bands of glycosaminoglycan (GAG) and collagen, GAG/Col, is calculated to evaluate the state of the cartilage tissue B in this embodiment. Instead of or in addition to this, the intensity ratio between other two types of Raman bands contained in the cartilage tissue B may be calculated.

As a first example of the two types of Raman bands, Raman bands of glycosaminoglycan (GAG) and protein are used. As the Raman band of protein, the Raman band of, for example, a protein phenylalanine residue having a peak in the proximity of 1003 $cm^{-1}$, as shown in FIG. 14, is selected. As the Raman band of glycosaminoglycan (GAG), the Raman band of, for example, sulfated glycosaminoglycan having a peak in the proximity of 1063 $cm^{-1}$ or in the proximity of 1380 $cm^{-1}$, as shown in FIG. 14, can be selected. Also, the intensity ratio between the Raman band of glycosaminoglycan (GAG) and the Raman band of protein (intensity of Raman band of GAG/intensity of Raman band of protein), GAG/Protein, is calculated.

In regenerated cartilage that is still in the process of regeneration and that has not matured into hyaline cartilage, as well as in fibrous cartilage and osteoarthritis cartilage tissue, the amount of glycosaminoglycan (GAG) decreases with respect to the total amount of protein in the cartilage tissue B. Therefore, the state of the cartilage tissue B can be evaluated on the basis of the intensity ratio GAG/Protein, which is proportional to the relative amount of glycosaminoglycan (GAG) with respect to the total amount of protein in the cartilage tissue B.

As a second example of the two types of Raman bands, Raman bands of collagen and protein are used. As the Raman band of collagen, instead of the above-described Raman bands at 921 $cm^{-1}$ and 815 $cm^{-1}$, a collagen amide III band from 1230 $cm^{-1}$ to 1240 $cm^{-1}$ or the collagen amide I band in the proximity of 1650 $cm^{-1}$ may be selected, as shown in FIG. 14. As the Raman band of protein, the Raman band of a protein phenylalanine residue having a peak in the proximity of 1003 $cm^{-1}$ is selected. Then, the intensity ratio between the Raman band of collagen and the Raman band of protein (intensity of Raman band of collagen/intensity of Raman band of protein), Col/Protein, is calculated. The state of the cartilage tissue B can also be evaluated by using the intensity ratio Col/Protein, acquired as described above, which is proportional to the relative amount of collagen with respect to the total amount of protein in the cartilage tissue B.

Figure 18:
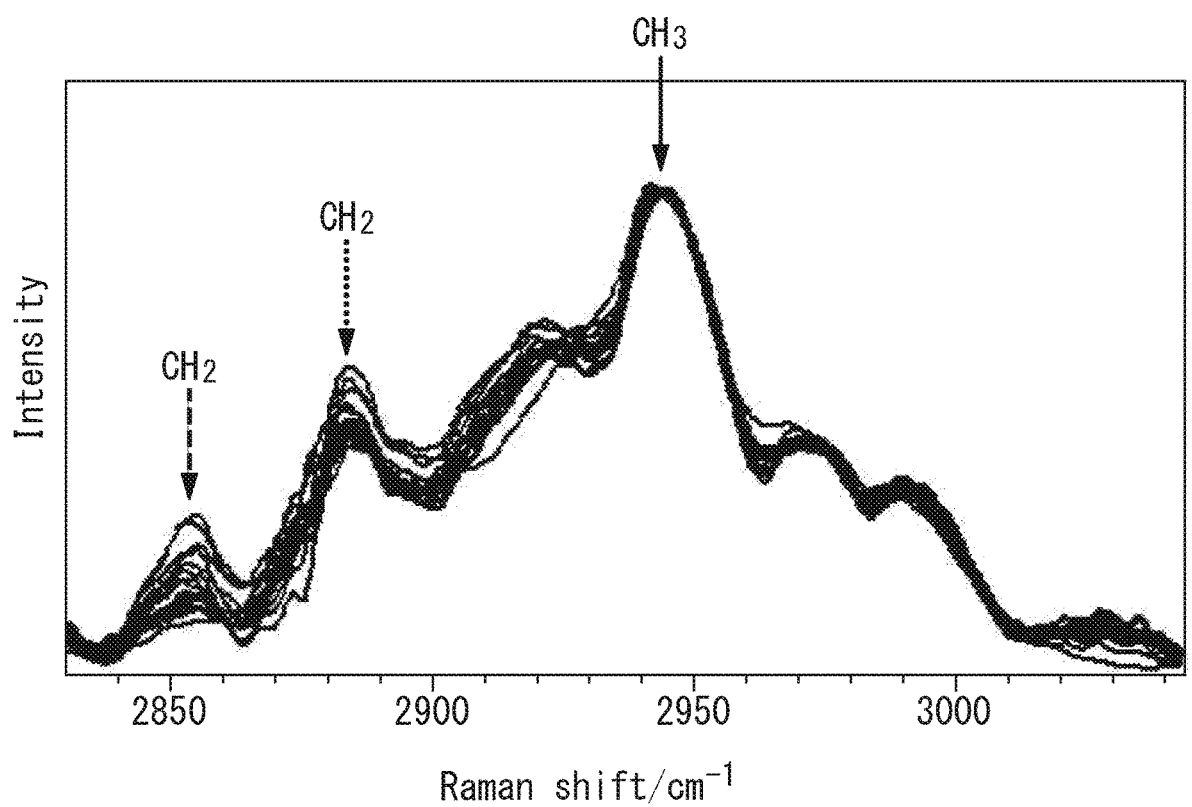
FIG. 18 is a diagram depicting a set of Raman spectra of cartilage tissue.

As a third example of the two types of Raman bands, Raman bands of a methyl group ($CH_3$) and a methylene group ($CH_2$) originating from protein and lipid in the cartilage tissue B can be used. FIG. 18 shows, of the Raman spectrum of the cartilage tissue B, a Raman shift range from 2830 $cm^{-1}$ to 3050 $cm^{-1}$, in which Raman bands of a methyl group and a methylene group appear.

As shown in FIG. 18, the band from 2940 to 2950 $cm^{-1}$ is selected as the Raman band of a methyl group, and the Raman band having a peak in the proximity of 2855 $cm^{-1}$ or in the proximity of 2885 $cm^{-1}$ is selected as the Raman band of methylene group. Then, the intensity ratio between the Raman band of a methylene group and the Raman band of a methyl group (Raman band intensity of methylene group/Raman band intensity of methyl group), $CH_2/CH_3$, is calculated.

Figure 19:
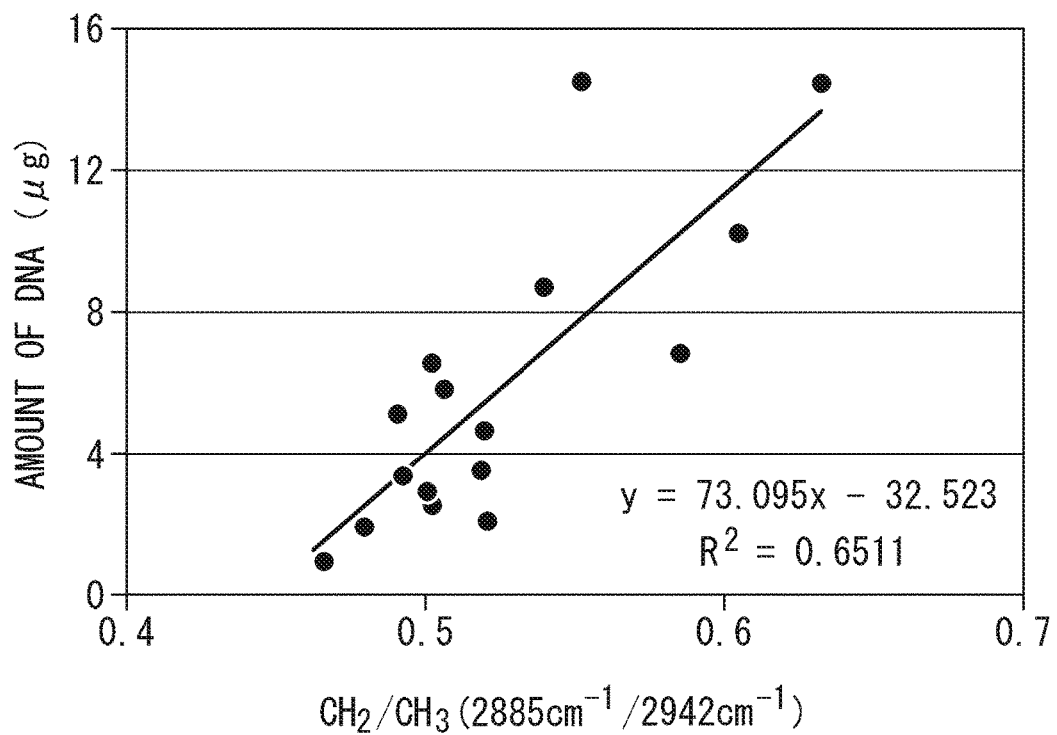
FIG. 19 is a graph showing the correlation between: the intensity ratio between Raman bands of a methyl group and a methylene group; and the amount of DNA in the cartilage tissue in the set of Raman spectra of cartilage tissue.

FIG. 19 shows a correlation between: the intensity ratio between the Raman bands of a methylene group and a methyl group, $CH_2/CH_3$; and the amount of DNA in the cartilage tissue (dry weight in 1-mg cartilage tissue). As shown in FIG. 19, because the intensity ratio $CH_2/CH_3$ had a high correlation with the amount of DNA in the cartilage tissue at a correlation coefficient of 0.8 or more, it was suggested that the Raman band of the methylene group originates from lipid in the cells.

Therefore, the state of cartilage in the process of regeneration or the state of osteoarthritis cartilage can be evaluated from the amount of cells in the cartilage tissue B that is estimated on the basis of the intensity ratio between the Raman bands of the methylene group and the methyl group, $CH_2/CH_3$.

As a fourth example of the two types of Raman bands, two split amide III bands having peaks in the proximity of 1240 $cm^{-1}$ and in the proximity of 1270 $cm^{-1}$ are used. It is known that the intensity ratio between these two split collagen amide III bands reflects a collagen molecular structure in the cartilage tissue B and changes as collagen degenerates. In osteoarthritis cartilage, the intensity ratio between these two split collagen amide III bands is known to indicate degeneration of type II collagen in hyaline cartilage, and thus, the degree of lesioning, such as osteoarthritis, involving degeneration of type II collagen in the cartilage tissue can be evaluated on the basis of the intensity ratio of these two amide III bands.

In this embodiment, in order to evaluate the state of cartilage tissue, the calculation unit 10 may calculate a feature quantity of the Raman spectrum reflecting the amount of a prescribed component contained in the cartilage tissue B or may quantitatively analyze the prescribed component itself by multivariate analysis of the Raman spectrum of the cartilage tissue B selected in step S7.

In a first example of the multivariate analysis, an arbitrary Raman shift range including the Raman band (1063 $cm^{-1}$ of sulfated glycosaminoglycan (GAG) is selected from the Raman spectrum of the cartilage tissue B, and the Raman spectrum in the selected range is subjected to multivariate analysis. For the multivariate analysis, for example, principal component analysis (PCA), principal component regression analysis (PCR), partial least squares analysis (PLS), or classical least squares analysis (CLS) is used.

Figure 20A:
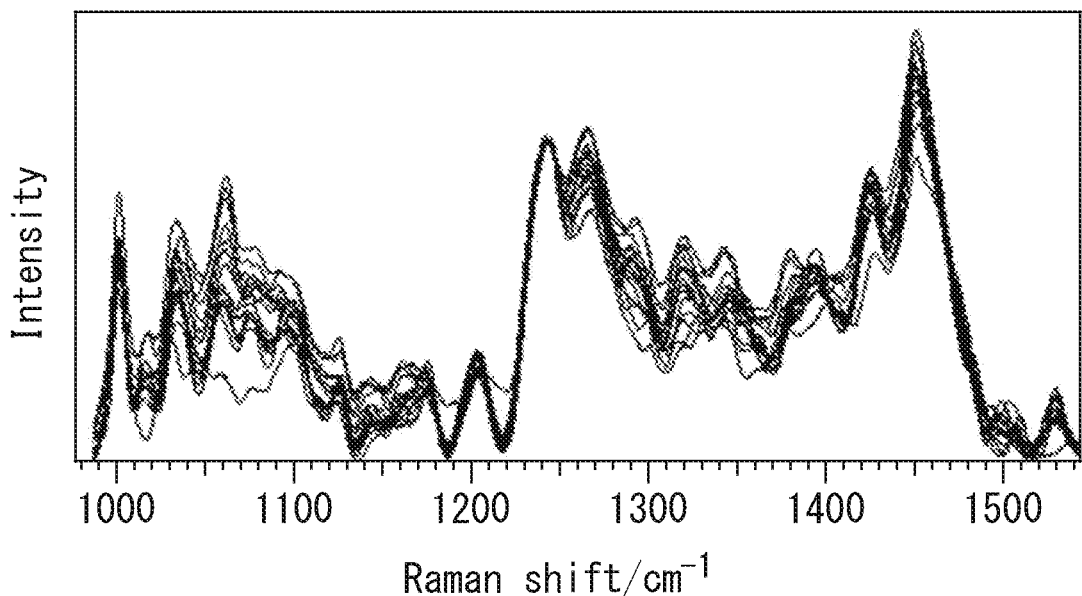
FIG. 20A is a diagram depicting a set of Raman spectra of cartilage tissue.
Figure 20B:
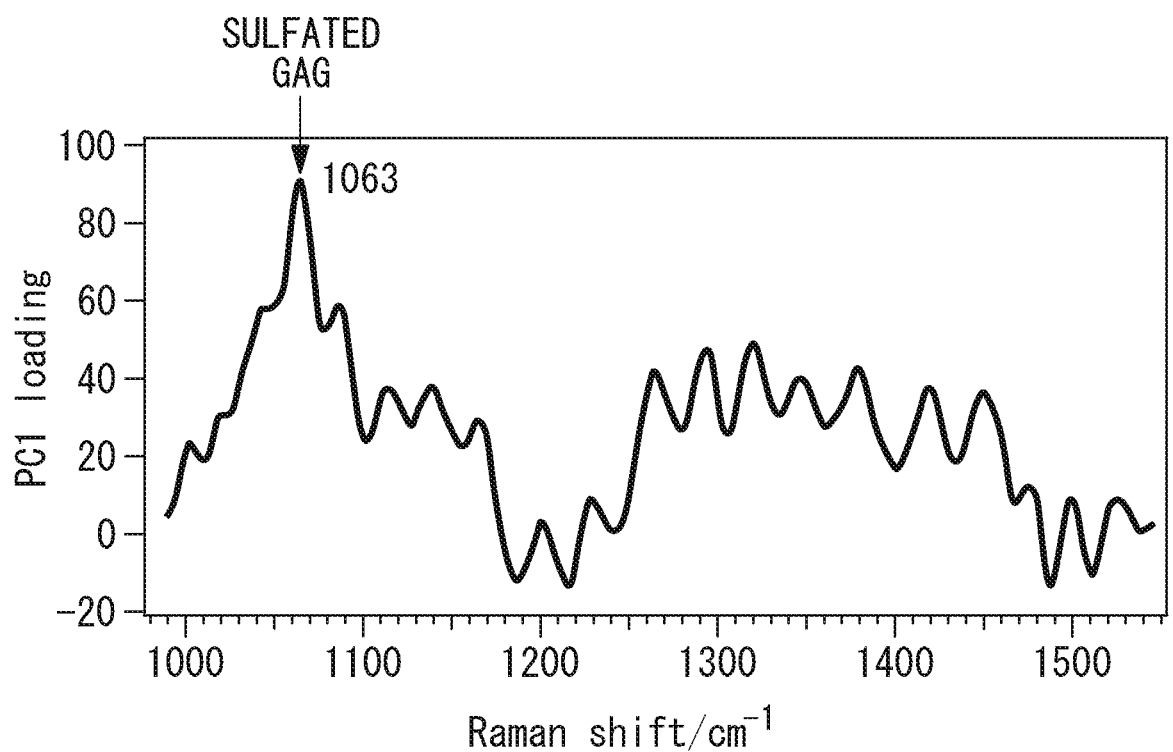
FIG. 20B is a diagram depicting a loading spectrum of a first principal component obtained by applying principal component analysis to the set of Raman spectra in FIG. 20A.
Figure 21:
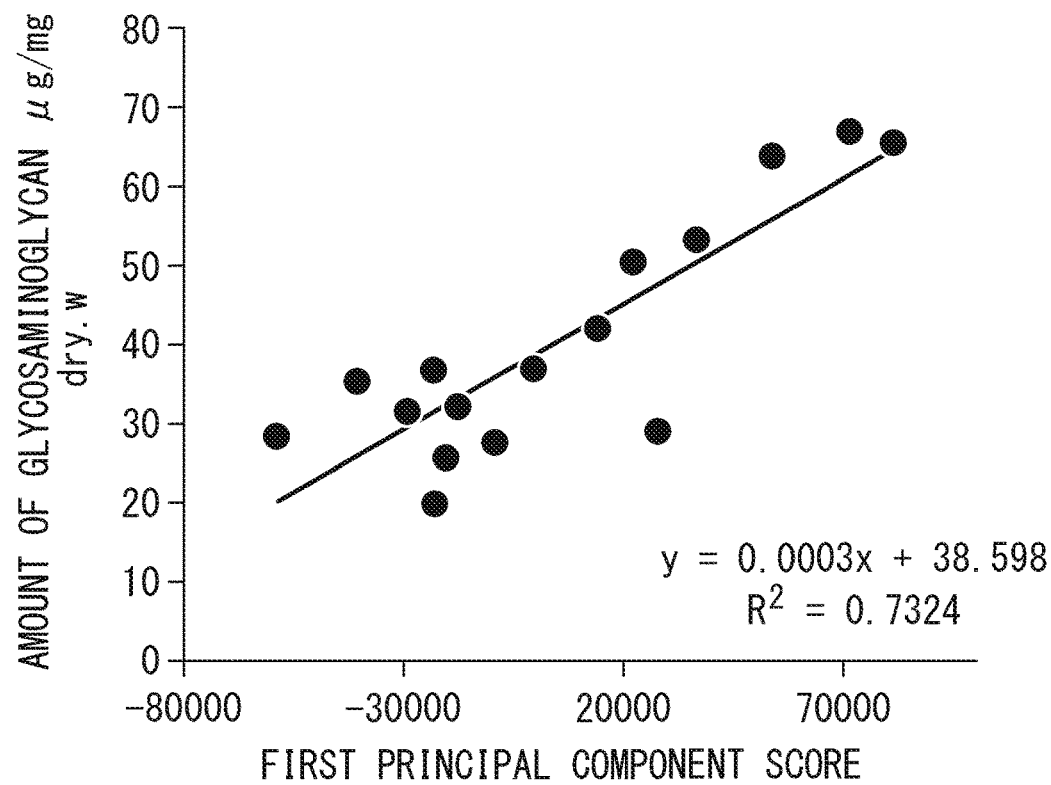
FIG. 21 is a graph showing the correlation between a first principal component score and the amount of sulfated glycosaminoglycan (GAG) in cartilage tissue.

Here, an example of principal component analysis will be described as an example of the multivariate analysis applied to Raman spectra of the cartilage tissues B in various states. FIG. 20A shows a set of Raman spectra of the cartilage tissues B in various states selected in step S7, and FIG. 20B shows a loading spectrum of a first principal component (first principal component waveform) obtained as a result of principal component analysis being applied to the set of Raman spectra in FIG. 20A. The loading spectrum of the first principal component has a large positive peak at a Raman shift value in the proximity of 1063 $cm^{-1}$ corresponding to the peak of the Raman band of sulfated glycosaminoglycan (GAG) and thus represents a signal originating from sulfated glycosaminoglycan. As shown in FIG. 21, there is a positive correlation between the magnitude of the score of the first principal component (first principal component score) obtained by projecting the set of Raman spectra in FIG. 20A onto the loading spectrum of this first principal component and the amount of sulfated glycosaminoglycan (GAG).

FIG. 21 shows the correlation between the first principal component score obtained by principal component analysis and the amount of sulfated glycosaminoglycan (GAG) contained per unit dry weight of the cartilage tissue. As is known from FIG. 21, a high correlation with a correlation coefficient of 0.86 was recognized between the first principal component score and the amount of sulfated glycosaminoglycan (GAG). In this manner, the state of the cartilage tissue B can be evaluated on the basis of the amount of sulfated glycosaminoglycan (GAG) by calculating the first principal component score in principal component analysis as a Raman spectrum feature quantity that correlates with the amount of sulfated glycosaminoglycan (GAG) in the cartilage tissue B.

A Raman spectrum analysis method based on another type of multivariate analysis may be used instead of principal component analysis.

For example, many mixture samples with different component ratios are prepared from isolates of sulfated glycosaminoglycan (GAG) and collagen (type II collagen), which are principal components of the cartilage tissue B, a Raman spectrum of each of the mixture samples is measured, and data representing the association between the component ratio and the corresponding Raman spectrum is produced for the mixture sample. Then, on the basis of this data, calibration curves of sulfated glycosaminoglycan (GAG) and type II collagen are generated by a regression analysis method, such as the partial least squares regression (PLS) analysis method or the principal component regression (PCR) method, and data on these calibration curves are stored in the memory unit 9. Thus, by measuring a Raman spectrum of an unknown cartilage tissue B, the relative amounts of sulfated glycosaminoglycan (GAG) and type II collagen can be estimated using the above-described calibration curves.

In a second example of the multivariate analysis, an arbitrary range of Raman shifts including the Raman bands of a methylene group (in the proximity of 2855 $cm^{-1}$ and in the proximity of 2885 $cm^{-1}$) is selected from the Raman spectrum of the cartilage tissue B, and the Raman spectrum in the selected range is subjected to multivariate analysis. As the multivariate analysis, for example, principal component analysis is used.

Figure 22A:
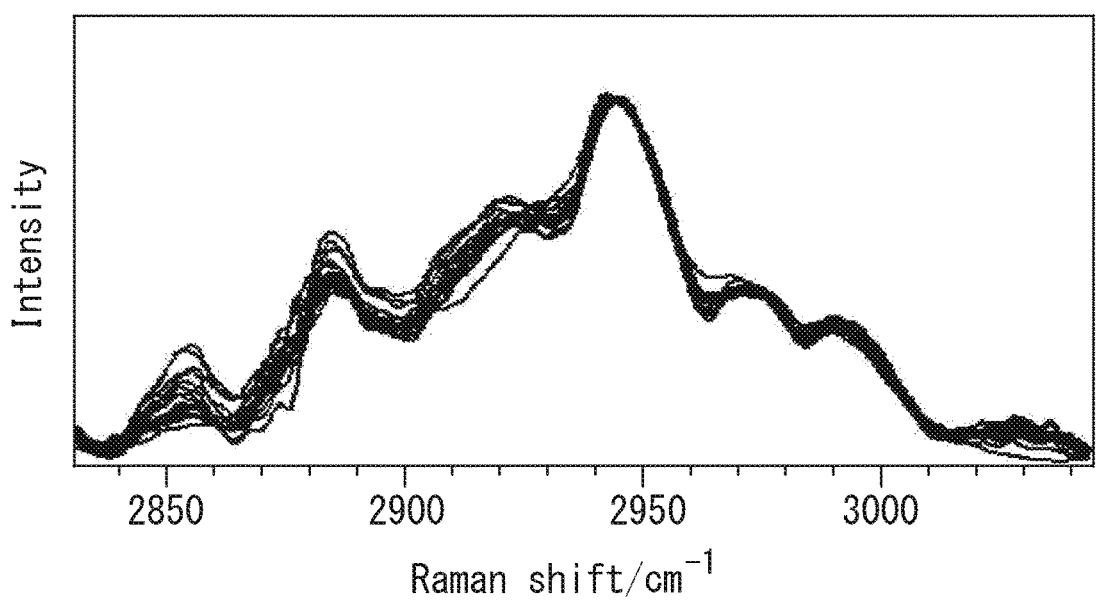
FIG. 22A is a diagram depicting a set of Raman spectra of cartilage tissue.
Figure 22B:
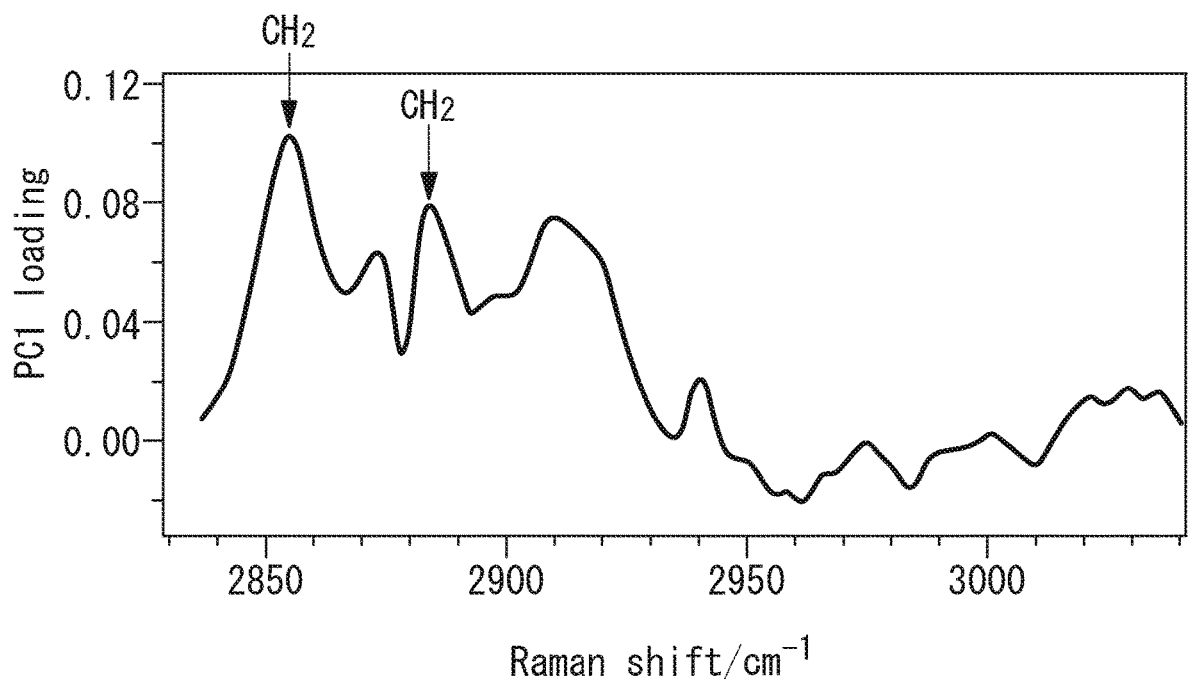
FIG. 22B is a diagram depicting a loading spectrum of a first principal component obtained by applying principal component analysis to the set of Raman spectra of cartilage tissue in FIG. 22A.
Figure 23:
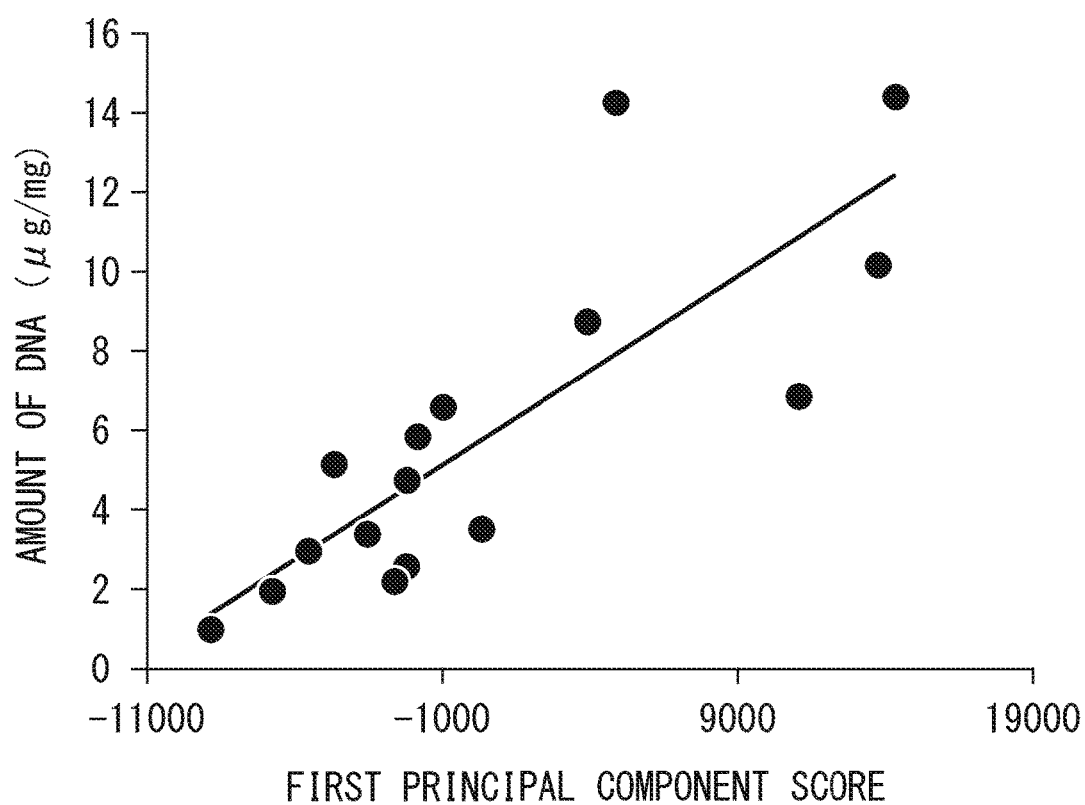
FIG. 23 is a graph showing the correlation between a first principal component score and the amount of DNA in cartilage tissue.

FIG. 22A shows a set of Raman spectra of the cartilage tissue B selected in step S7, and FIG. 22B shows a loading spectrum of a first principal component (first principal component waveform) obtained as a result of principal component analysis being applied to the set of Raman spectra in FIG. 22A. The loading spectrum of the first principal component has large positive peaks at Raman shift values of 2855 $cm^{-1}$ and 2885 $cm^{-1}$ corresponding to the peaks of the Raman bands of a methylene group, and it is suggested that this loading spectrum is a spectrum including a contribution made by lipid contained in the cartilage tissue B. As shown in FIG. 23, it is clear that there is a positive correlation between the magnitude of the first principal component score obtained by projecting the set of Raman spectra in FIG. 22A onto the loading spectrum of this first principal component and the amount of DNA in the cartilage tissue B. Thus, these Raman bands of a methylene group are considered to originate from lipid in the cartilage cell B.

FIG. 23 shows the correlation between the first principal component score obtained by principal component analysis and the amount of DNA (DNA dry weight in 1-milligram cartilage tissue) in the cartilage tissue B. A high correlation with a correlation coefficient of 0.82 is recognized between the first principal component score in principal component analysis and the amount of DNA in the cartilage tissue B. In this manner, the state of cartilage in the process of regeneration or the state of osteoarthritis cartilage in the cartilage tissue B can be evaluated on the basis of the amount of cells by calculating the first principal component score in principal component analysis as a Raman spectrum feature quantity that correlates with the amount of cells in the cartilage tissue B.

In this embodiment, the calculation unit 10 may further estimate the thickness of the cartilage tissue B on the basis of the first and second Raman spectra.

More specifically, the calculation unit 10 calculates the intensity ratio between a Raman band originating from the cartilage tissue B and a Raman band originating from the subchondral bone tissue C in each of the first and second Raman spectra, as defined in the following expression:

Intensity ratio=intensity of Raman band originating from subchondral bone tissue/intensity of Raman band originating from cartilage tissue Here, the Raman band of hydroxyapatite (HAP) having a peak in the proximity of a Raman shift value of 958 $cm^{-1}$ can be used as the Raman band originating from the subchondral bone tissue C, and the Raman band of type II collagen having a peak in the proximity of a Raman shift value of 921 $cm^{-1}$ or in the proximity of a Raman shift value of 815 $cm^{-1}$ can be used as the Raman band originating from the cartilage tissue B.

Figure 24:
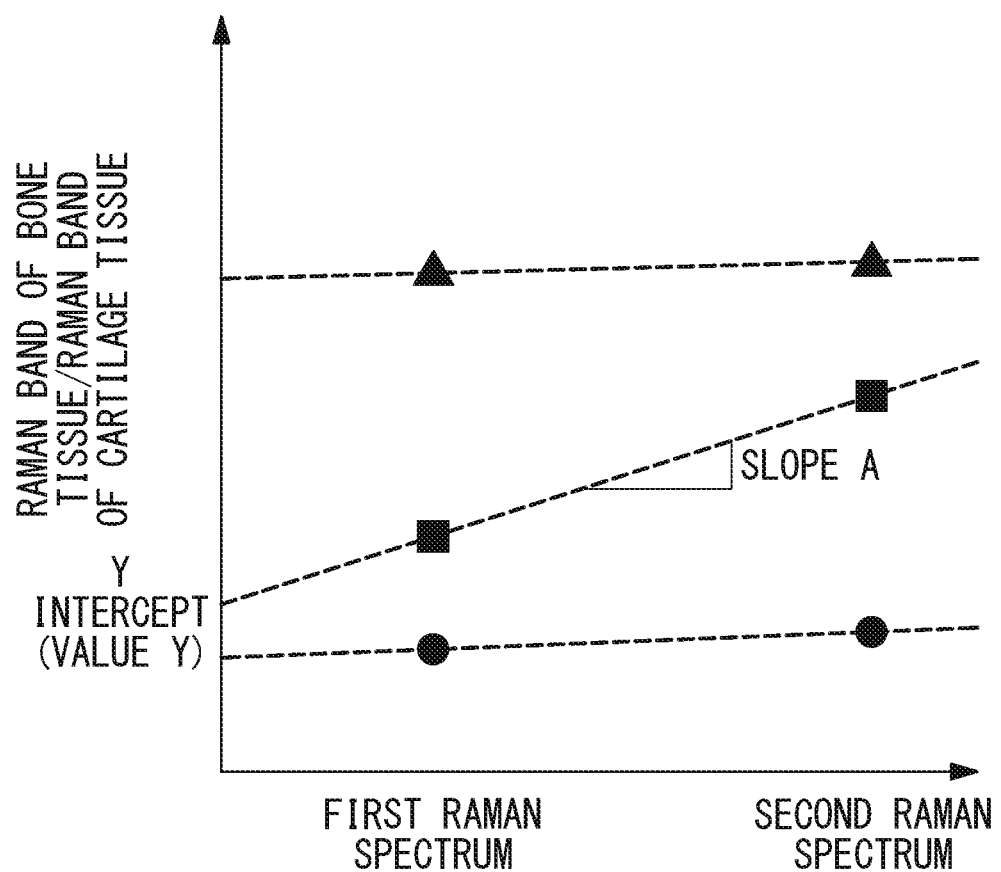
FIG. 24 is graph showing the relationship between the thicknesses of various types of cartilage tissue and the intensity ratios between the Raman bands of hydroxyapatite (HAP) and collagen (Col), HAP/Col, in the first and second Raman spectra.

FIG. 24 is a diagram in which the intensity ratios calculated from the first Raman spectra and the intensity ratios calculated from the second Raman spectra are plotted after Raman spectra of cartilage tissues with different thicknesses are acquired. The calculation unit 10 further calculates values Y of the Y intercepts and the slopes A of the straight lines each passing through two plots indicating the intensity ratio of the first Raman spectrum and the intensity ratio of the second Raman spectrum.

Here, in the case where the thickness of the cartilage tissue B is large enough, as shown in FIG. 11A, to include the examination area F1 and the examination area F2 (refer to the round plots in FIG. 24), both the value Y and the slope A become small. In addition, in the case where the cartilage tissue B is so thin, as shown in FIG. 12A, that the cartilage tissue B barely includes the examination area F1 and the examination area F2 (refer to the triangular plots in FIG. 24), the value Y becomes large and the slope A becomes small. In addition, in the case where the thickness of the cartilage tissue B is between the above-described two cases (refer to the rectangular plots in FIG. 24), the value Y becomes small and the slope A becomes large.

In this manner, the values (Y, A) change according to the relative thickness of the cartilage tissue B in relation to the examination area F1 and the examination area F2. Therefore, the thickness of the cartilage tissue B in an unknown epiphysis can be estimated as follows. A database is produced by establishing the relationship between the actual thicknesses of cartilage tissues B and the corresponding values (Y, A) and is stored in the memory unit 9. The calculation unit 10 reads out this database from the memory unit 9, obtains the values (Y, A) from the database on the basis of the intensity ratio between two Raman bands calculated from each of the first and second Raman spectra of the unknown epiphysis, and estimates the thickness of the cartilage tissue B of the unknown epiphysis from the obtained values (Y, A).

The thickness of the cartilage tissue B can be estimated as follows.

Figure 25:
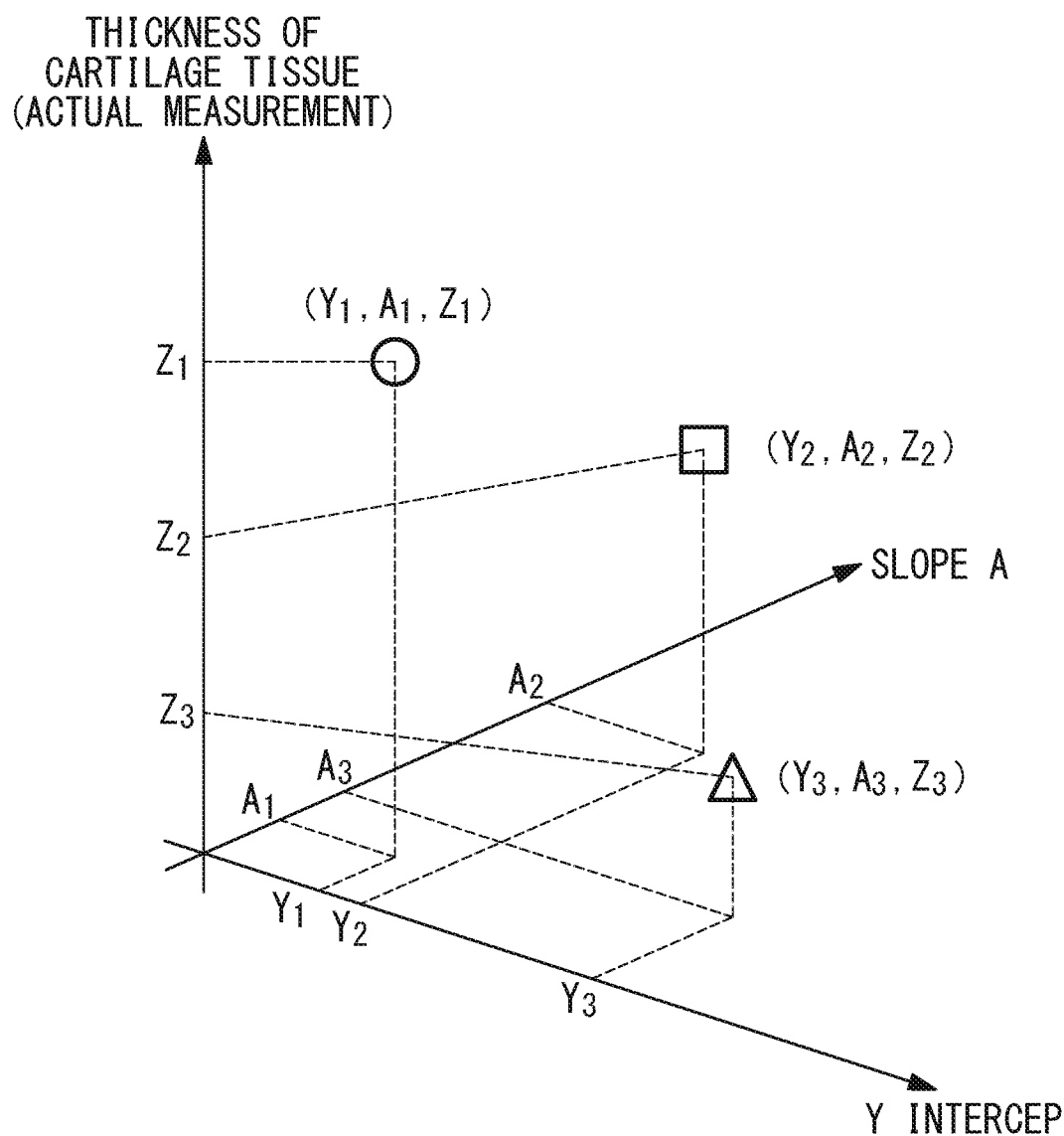
FIG. 25 is a diagram for illustrating a method of producing teaching data for estimating the thickness of cartilage tissue B, showing a three-dimensional coordinate system where the Y-intercept Y and the slope A of the graph in FIG. 24 and the thickness of cartilage tissue constitute axes of the coordinate system.

Intensity ratios are obtained from the first and second Raman spectra for cartilages in various states, and values (Y, A) are further obtained by performing plotting as shown in FIG. 24. At the same time, coordinate points (Y, A, Z) in a three-dimensional coordinate system as shown in FIG. 25 are plotted by measuring the thicknesses Z of the cartilage tissues, where the coordinate axes correspond to the value Y of the Y intercept, the slope A, and the thickness Z of the cartilage tissue, respectively. For example, three points ($Y_1$, $A_1$, $Z_1$), ($Y_2$, $A_2$, $Z_2$), and ($Y_3$, $A_3$, $Z_3$) can be plotted in the three-dimensional space for three types of cartilage tissue with different tissue thicknesses. After such coordinate points, serving as teaching data, are acquired from many types of cartilage tissue, it is sufficient to calculate an estimated thickness plane (flat plane or curved plane) through calculation based on spatial interpolation so that the thickness Z of cartilage tissue corresponding to any values (Y, A) can be estimated. If such an estimated thickness plane has been preliminarily calculated, the cartilage thickness at an observation point can be estimated merely by measuring Raman spectra of an unknown epiphysis and by calculating values (Y, A) from the first and second Raman spectra. As an estimation method based on such spatial interpolation, a spatial statistics method, such as Kriging interpolation, may be used.

Because the thickness of the cartilage tissue B can change depending on the maturation degree of regenerated cartilage in the process of regeneration or the progression stage of osteoarthritis, the states of regenerated cartilage tissue and osteoarthritis cartilage tissue can be determined by estimating the thickness of the cartilage tissue B. The thickness of the cartilage tissue B estimated by the above-described method may be displayed on the display unit 11, or alternatively, a classification index that is graded so as to correlate the state of the cartilage tissue B with the thickness of the cartilage tissue B may be displayed on the display unit 11.

A data set of (Y, A) may be obtained from many types of the epiphysis A, and, on the basis of this obtained data set, a calibration curve for correlating the thicknesses of the cartilage tissue B with the Y intercepts and the slopes A may be preliminarily produced by a regression analysis method, such as the principal component regression method (PCR) or the partial least squares method (PLS), thereby estimating the thickness of the cartilage tissue B of an unknown epiphysis from Raman spectrum data of the unknown epiphysis by using this calibration curve.

Alternatively, the thickness of the cartilage tissue B may be estimated by multivariate analysis of the Raman spectrum. More specifically, for many samples of the epiphysis A with different thicknesses of the cartilage tissue B, first and second Raman spectra are acquired within a range covering the Raman band of hydroxyapatite having a Raman shift value in the proximity of 958 $cm^{-1}$ and the Raman band of type II collagen having a Raman shift value in the proximity of 921 $cm^{-1}$, and then the intensity ratio between the Raman band of collagen and the Raman band of hydroxyapatite (HAP) is calculated from each of the first and second Raman spectra for each of the samples, in the same manner as in steps S4 and S5. Furthermore, for each of the samples, the sum of the Raman band intensity ratio in the first Raman spectrum and the Raman band intensity ratio in the second Raman spectrum is calculated, and data in which this sum of the Raman band intensity ratios is associated with the actual thickness of the cartilage tissue is produced. Then, on the basis of this data, a calibration curve for the thicknesses of the cartilage tissue is generated by a regression analysis method, such as the PLS analysis method or the PCR analysis method, and this calibration curve is stored in the memory unit 9.

By doing so, the thickness of the cartilage tissue can be estimated from the first and second Raman spectra of an unknown epiphysis.

The above-described control unit 8 and the calculation unit 10 of the cartilage-tissue analysis device 100 are realized by, for example, a computer including: a central processing unit (CPU); an auxiliary storage device, such as an HDD, for storing a control program and an arithmetic operation program that cause the CPU to execute the processes executed by the above-described control unit 8 and calculation unit 10; and a main storage device, such as a RAM or a ROM, functioning as a working area of the CPU. The memory unit 9 is realized by, for example, the main storage device.

As a result, the above-described embodiment leads to the following aspect.

One aspect of the present invention is a cartilage-tissue analysis device including: a laser light source for outputting laser light; an illuminating fiber having a light-emission surface at a distal end thereof, said illuminating fiber emitting, from the light-emission surface towards biological tissue including cartilage tissue, the laser light that is incident thereon from the laser light source; a first light-collecting fiber and a second light-collecting fiber each having a light-receiving surface at a distal end thereof and each receiving scattered light from the biological tissue at the light-receiving surface; a detection unit that detects a first Raman spectrum from the scattered light received by the first light-collecting fiber and that detects a second Raman spectrum from the scattered light received by the second light-collecting fiber; an intensity-ratio calculation unit for calculating, from each of the first Raman spectrum and the second Raman spectrum detected by the detection unit, an intensity ratio between a Raman band originating from the cartilage tissue and a Raman band originating from subchondral bone tissue; and an evaluation unit that selects, from among the first Raman spectrum and the second Raman spectrum, a Raman spectrum the intensity ratio of which is within a prescribed range, said intensity ratio being calculated by the intensity-ratio calculation unit, and that evaluates a state of the cartilage tissue by analyzing the selected Raman spectrum, wherein the distance from the light-emission surface to the light-receiving surface of the first light-collecting fiber differs from the distance from the light-emission surface to the light-receiving surface of the second light-collecting fiber.

According to this aspect, the illuminating fiber is supplied with laser light from the laser light source. When the laser light is radiated from the light-emission surface to the biological tissue, scattered light of the biological tissue generated in an illumination region of the laser light is received by the first and second light-collecting fibers, and first and second Raman spectra are acquired by the detection unit from the scattered light received by the first and second light-collecting fibers. At this time, the first and second Raman spectra include Raman spectra only from the cartilage tissue located in the epiphysis surface layer or Raman spectra from both the cartilage tissue and the subchondral bone tissue located underneath the cartilage tissue.

In this case, because the light-receiving surface of the first light-collecting fiber and the light-receiving surface of the second light-collecting fiber are disposed at positions the distances from which to the light-emission surface of the illuminating fiber differ from each other, the first light-collecting fiber and the second light-collecting fiber receive scattered light from areas different from each other in the depth direction (laser light irradiation direction) within the illumination region of the laser light. Therefore, the proportion of the contribution made by the cartilage tissue to the first Raman spectrum can differ from the proportion of the contribution made by the cartilage tissue to the second Raman spectrum.

Here, by calculating the intensity ratio between a Raman band originating from a cartilage tissue component and a Raman band originating from a subchondral bone tissue component in each of the first Raman spectrum and the second Raman spectrum, it is possible to estimate the proportion of the contribution made by the cartilage tissue to each of these Raman spectra. Therefore, on the basis of the calculated intensity ratio, the first Raman spectrum or the second Raman spectrum, whichever includes a Raman spectrum only from the cartilage tissue or a Raman spectrum to which the cartilage tissue contributes with a large proportion, can be selected. Then, by using the selected Raman spectrum, in which information on the Raman spectrum originating from the subchondral bone tissue is excluded as much as possible, the state of the cartilage tissue can be evaluated with high accuracy.

In the above-described aspect, when the intensity ratio is calculated, the intensity-ratio calculation unit may use the intensity of a Raman band of type II collagen as the Raman band originating from the cartilage tissue and may use the intensity of a Raman band of hydroxyapatite as the Raman band originating from the subchondral bone tissue. Alternatively, in the above-described aspect, when the intensity ratio is calculated, the intensity-ratio calculation unit may use the intensity of a Raman band of glycosaminoglycan (GAG) as the Raman band originating from the cartilage tissue and may use the intensity of a Raman band of hydroxyapatite as the Raman band originating from the subchondral bone tissue.

By doing so, the proportion of the contribution made by the cartilage tissue and the proportion of the contribution made by the subchondral bone tissue in the first and second Raman spectra can be calculated with high accuracy.

In the above-described aspect, the evaluation unit may calculate an intensity ratio between two types of Raman bands that originate from the cartilage tissue and that have Raman shifts different from each other in the selected Raman spectrum and may evaluate the state of the cartilage tissue on the basis of the calculated intensity ratio.

Because the intensity of a Raman band from each component contained in the cartilage tissue is proportional to the content of that component, the intensity ratio between Raman bands of two different types of components reflects the relative amounts of the two different types of components. Alternatively, it is known that the intensity ratio between two types of Raman bands, of a prescribed component, having mutually different Raman shifts reflects the molecular structure of that component.

Therefore, for a component contained in the cartilage tissue, information on the relative amount of that component and a change in the molecular structure of that component, i.e., degeneration of the cartilage matrix molecules, can be obtained from the calculated intensity ratio between the Raman bands. On the basis of such information, cartilage lesioning typified by osteoarthritis (OA) and a biochemical state of the cartilage tissue, such as the maturation degree of regenerated cartilage, can be evaluated.

In the above-described aspect, the two types of Raman bands may be a Raman band of collagen and a Raman band of glycosaminoglycan (GAG). This glycosaminoglycan is sulfated glycosaminoglycan, such as chondroitin sulfate and keratan sulfate, which is major glycosaminoglycan contained in the cartilage tissue.

Here, the intensity ratio between the Raman band of collagen and the Raman band of glycosaminoglycan (GAG) reflects the relative amount of glycosaminoglycan (GAG) with respect to collagen contained in the cartilage tissue.

Therefore, on the basis of the calculated intensity ratio, lesioning of the cartilage tissue characterized by a change in the amount of glycosaminoglycan (GAG) can be evaluated. In addition, because glycosaminoglycan (GAG) is contained in a large amount in hyaline cartilage but is barely contained in fibrous cartilage, the amount of glycosaminoglycan (GAG) in the cartilage tissue in the process of regeneration differs depending on whether the cartilage tissue is hyaline cartilage, fibrous cartilage, or a mixture of hyaline cartilage and fibrous cartilage. Therefore, on the basis of the amount of glycosaminoglycan (GAG) in the cartilage tissue, the maturation state of the cartilage tissue in the process of regeneration can be evaluated.

In the above-described aspect, the two types of Raman bands may be a Raman band of amino acid contained in protein in an extracellular matrix, such as collagen and proteoglycan, and in cartilage cells and a Raman band of glycosaminoglycan (GAG).

The intensity ratio between the Raman band of protein amino acid and the Raman band of glycosaminoglycan (GAG) reflects the relative amount of glycosaminoglycan (GAG) with respect to the total amount of protein in the cartilage tissue. Therefore, on the basis of the calculated intensity ratio, lesioning of the cartilage tissue characterized by a change in the amount of glycosaminoglycan (GAG) can be evaluated. In addition, on the basis of the amount of glycosaminoglycan (GAG), the maturation state of the cartilage in the process of regeneration can be evaluated.

In the above-described aspect, the two types of Raman bands may be a Raman band of amino acid contained in protein in an extracellular matrix, such as collagen and proteoglycan, and in cartilage cells and a Raman band of collagen.

The intensity ratio between the Raman band of protein amino acid and the Raman band of collagen reflects the relative amount of collagen with respect to the total amount of protein in the cartilage tissue. Therefore, on the basis of the calculated intensity ratio, lesioning of the cartilage tissue involving a change in the amount of collagen can be evaluated. In addition, of the collagen in the cartilage tissue in the process of regeneration, the amount of type II collagen varies depending on whether the cartilage tissue is normal hyaline cartilage, poor fibrous cartilage as regenerated cartilage, or cartilage in the process of regeneration. Therefore, on the basis of the amount of collagen, the maturation state of the cartilage in the process of regeneration can be evaluated.

In the above-described aspect, the two types of Raman bands may be a Raman band of a methylene group and a Raman band of a methyl group contained in protein or lipid in an extracellular matrix, such as collagen and proteoglycan, and in cartilage cells.

The intensity ratio between the Raman band of a methylene group and the Raman band of a methyl group correlates with relative amount of cells contained in the cartilage tissue. Therefore, on the basis of the calculated intensity ratio, the maturation state of the cartilage in the process of regeneration can be evaluated.

In the above-described aspect, the two types of Raman bands may be Raman bands of amide III in collagen.

Collagen amide III appears as Raman bands having two peaks, one at a small wave number in the proximity of 1240 $cm^{-1}$ and the other at a large wave number in the proximity of 1260 $cm^{-1}$, within a Raman shift range from 1230 to 1280 $cm^{-1}$. It is known that the intensity ratio between the two Raman bands of this amide III, i.e., the Raman band on the small wave number side and the Raman band on the large wave number side, reflects a change in the molecular structure characterized by the secondary structure of collagen in the cartilage tissue. It is also known that lesioning of the cartilage tissue, such as osteoarthritis, is characterized by degeneration of type II collagen, i.e., a change in the molecular structure, in the cartilage tissue. Therefore, on the basis of the calculated intensity ratio between the amide III Raman bands, lesioning of the cartilage tissue, such as osteoarthritis, characterized by collagen denaturation can be evaluated.

In the above-described aspect, by applying multivariate analysis, such as principal component analysis (PCA), principal component regression analysis (PCR), or partial least squares analysis (PLS), to the selected Raman spectra, the evaluation unit may calculate a feature quantity of the Raman spectra by multivariate analysis, said feature quantity correlating with the amount of glycosaminoglycan (GAG), collagen, or cells contained in the cartilage tissue, or may estimate the amount of glycosaminoglycan (GAG), collagen, or cells contained in the cartilage tissue, thus evaluating the state of the cartilage tissue on the basis of the obtained feature quantity of the Raman spectra or the amount of glycosaminoglycan (GAG), collagen, or cells.

By doing so, it is possible to evaluate the degree of growth of regenerated cartilage and lesioning of the cartilage tissue, such as osteoarthritis, characterized by a change in the amount of glycosaminoglycan or tissue degeneration typified by collagen denaturation.

In the above-described aspect, from each of the first Raman spectrum and the second Raman spectrum, the evaluation unit may calculate an intensity ratio between a Raman band originating from the cartilage tissue and a Raman band originating from the subchondral bone tissue and may estimate the thickness of the cartilage tissue on the basis of the two calculated intensity ratios, as well as a prepared calibration curve or a statistical estimation method for correlating the intensity ratio between the Raman bands of the cartilage tissue and the subchondral bone tissue with the thickness of the cartilage tissue.

By doing so, it is possible to evaluate the thickness of the cartilage tissue on the basis of the calculated intensity ratio between two Raman bands, i.e., the Raman band of the cartilage tissue and the Raman band of the subchondral bone tissue.

The present invention affords an advantage in that a Raman spectrum originating from cartilage tissue and a Raman spectrum originating from subchondral bone tissue can be separated from a Raman spectrum of an epiphysis composed of the cartilage tissue and the subchondral bone tissue, the Raman spectrum originating from the cartilage tissue can be selectively acquired, and the Raman spectrum originating from the cartilage tissue can be analyzed, thereby making it possible to evaluate, with high accuracy, the state of the cartilage tissue that is present in the surface layer of the epiphysis.

REFERENCE SIGNS LIST

1 Laser light source
3 Spectrometer (detection unit)
5 Photodetector (detection unit)
6 Illuminating fiber
71 First light-collecting fibers
72 Second light-collecting fibers
10 Calculation unit (intensity-ratio calculation unit, evaluation unit)
100 Cartilage-tissue analysis device
A Epiphysis
B Cartilage tissue
C Subchondral bone tissue

The invention claimed is:

1. A cartilage-tissue analysis device for analyzing a first Raman spectrum and a second Raman spectrum,
   wherein a detector is configured to detect the first Raman spectrum from scattered light from a biological tissue, including cartilage tissue, received by a light-receiving surface at a distal end of a first light-collecting fibers,
   wherein the detector is configured to detect the second Raman spectrum from the scattered light from the biological tissue received by a light-receiving surface at a distal end of a second light-collecting fibers,
   wherein the biological tissue scatters laser light emitted towards the biological tissue from a light-emission surface at a distal end of an illuminating fiber as the scattered light, and
   wherein each of the first and the second Raman spectra includes a first Raman band corresponding to the cartilage tissue and a second Raman band corresponding to subchondral bone tissue,
   the cartilage-tissue analysis device comprising:
   one or more processors each comprising hardware, wherein the one or more processors are configured to:
   calculate a first intensity ratio between the first Raman band and the second Raman band of the first Raman spectrum;
   determine whether the first intensity ratio is greater than a predetermined threshold;
   in response to determining that the first intensity ratio is greater than the predetermined threshold, select the first Raman spectrum;
   calculate a second intensity ratio between the first Raman band and the second Raman band of the second Raman spectrum;
   determine whether the second intensity ratio is greater than the predetermined threshold;
   in response to determining that the second intensity ratio is greater than the predetermined threshold, select the second Raman spectrum; and
   evaluate a state of the cartilage tissue by analyzing the one or more the first Raman spectrum selected and the second Raman spectrum selected.

2. The cartilage-tissue analysis device according to claim 1, wherein, when the first intensity ratio or the second intensity ratio is calculated, the calculating of the first intensity ratio or the second intensity ratio uses an intensity of a Raman band of type II collagen as the Raman band corresponding to the cartilage tissue and uses an intensity of a Raman band of hydroxyapatite as the Raman band corresponding to the subchondral bone tissue.

3. The cartilage-tissue analysis device according to claim 1, wherein, when the first intensity ratio or the second intensity ratio is calculated, the calculating of the first intensity ratio or the second intensity ratio uses an intensity of a Raman band of glycosaminoglycan as the Raman band corresponding to the cartilage tissue and uses an intensity of a Raman band of hydroxyapatite as the Raman band corresponding to the subchondral bone tissue.

4. The cartilage-tissue analysis device according to claim 1, wherein the evaluating of the state of the cartilage tissue calculates an intensity ratio between two types of Raman bands that originate from the cartilage tissue and that have Raman shifts different from each other in the selected Raman spectrum and evaluates the state of the cartilage tissue on a basis of the calculated intensity ratio.

5. The cartilage-tissue analysis device according to claim 4, wherein the two types of Raman bands are a Raman band of collagen and a Raman band of glycosaminoglycan.

6. The cartilage-tissue analysis device according to claim 4, wherein the two types of Raman bands are a Raman band of amino acid contained in proteins and a Raman band of glycosaminoglycan.

7. The cartilage-tissue analysis device according to claim 4, wherein the two types of Raman bands are a Raman band of amino acid contained in proteins and a Raman band of collagen.

8. The cartilage-tissue analysis device according to claim 4, wherein the two types of Raman bands are a Raman band of a methylene group and a Raman band of a methyl group.

9. The cartilage-tissue analysis device according to claim 4, wherein the two types of Raman bands are Raman bands of amide III in collagen.

10. The cartilage-tissue analysis device according to claim 1, wherein, by performing multivariate analysis of the selected Raman spectra, evaluating the state of the cartilage tissue estimates an amount of glycosaminoglycan contained in the cartilage tissue or calculates a feature quantity of the Raman spectra by multivariate analysis, said feature quantity correlating with the amount of glycosaminoglycan, and evaluates the state of the cartilage tissue on a basis of the obtained amount of glycosaminoglycan or the feature quantity of the Raman spectra.

11. The cartilage-tissue analysis device according to claim 1, wherein, by performing multivariate analysis of the selected Raman spectra, evaluating of the state of the cartilage tissue estimates an amount of collagen contained in the cartilage tissue or calculates a feature quantity of the Raman spectra by multivariate analysis, said feature quantity correlating with the amount of collagen, and evaluates the state of the cartilage tissue on a basis of the obtained amount of collagen or the feature quantity of the Raman spectra.

12. The cartilage-tissue analysis device according to claim 1, wherein, by performing multivariate analysis of the selected Raman spectra, evaluating of the state of the cartilage tissue estimates an amount of cells contained in the cartilage tissue or calculates a feature quantity of the Raman spectra by multivariate analysis, said feature quantity correlating with the amount of cells, and evaluates the state of the cartilage tissue on a basis of the obtained amount of cells or the feature quantity of the Raman spectra.

13. The cartilage-tissue analysis device according to claim 1, wherein, from each of the first Raman spectrum and the second Raman spectrum, the evaluating of the state of the cartilage tissue calculates an intensity ratio between a Raman band originating from the cartilage tissue and a Raman band originating from the subchondral bone tissue and estimates the thickness of the cartilage tissue on a basis of the two calculated intensity ratios.

14. The cartilage-tissue analysis system comprising:
the cartilage-tissue analysis device according to claim 1;
the illuminating fiber;
the first light-collecting fiber;
the second light-collecting fiber; and
the detector.

15. A non-transitory computer-readable storage device storing instructions for analyzing a first Raman spectrum and a second Raman spectrum,
wherein a detector is configured to detect the first Raman spectrum from scattered light from a biological tissue, including cartilage tissue, received by a light-receiving surface at a distal end of a first light-collecting fiber,
wherein the detector is configured to detect the second Raman spectrum from the scattered light from the biological tissue received by a light-receiving surface at a distal end of a second light-collecting fiber,
wherein the biological tissue scatters laser light emitted towards the biological tissue from a light-emission surface at a distal end of an illuminating fiber as the scattered light, and
wherein each of the first and the second Raman spectra includes a first Raman band corresponding to the cartilage tissue and a second Raman band corresponding to subchondral bone tissue,
the instructions causing a computer to perform, at least:
calculate a first intensity ratio between the first Raman band and the second Raman band of the first Raman spectrum;
determine whether the first intensity ratio is greater than a predetermined threshold;
in response to determining that the first intensity ratio is greater than the predetermined threshold, select the first Raman spectrum;
calculate a second intensity ratio between the first Raman band and the second Raman band of the second Raman spectrum;
determine whether the second intensity ratio is greater than the predetermined threshold;
in response to determining that the second intensity ratio is greater than the predetermined threshold, select the second Raman spectrum; and
evaluate a state of the cartilage tissue by analyzing the one or more the first Raman spectrum selected and the second Raman spectrum selected.

* * * * *